(12) United States Patent
Ogawa et al.

(10) Patent No.: US 10,006,923 B2
(45) Date of Patent: Jun. 26, 2018

(54) METHOD FOR MEASURING GLYCATED HEMOGLOBIN

(71) Applicants: KYOWA MEDEX CO., LTD., Tokyo (JP); Kyoto University, Kyoto (JP)

(72) Inventors: Noriyuki Ogawa, Shizuoka (JP); Fumi Umehara, Shiuoka (JP); Takehide Kimura, Tokyo (JP); Kousaku Murata, Kyoto (JP); Wataru Hashimoto, Kyoto (JP)

(73) Assignees: KYOWA MEDEX CO., LTD., Tokyo (JP); KYOTO UNIVERSITY, Kyoto (JP)

(*) Notice: Subject to any disclaimer, the term of this patent is extended or adjusted under 35 U.S.C. 154(b) by 0 days. days.

(21) Appl. No.: 14/897,907

(22) PCT Filed: Jul. 7, 2014

(86) PCT No.: PCT/JP2014/068010
§ 371 (c)(1),
(2) Date: Dec. 11, 2015

(87) PCT Pub. No.: WO2015/005257
PCT Pub. Date: Jan. 15, 2015

(65) Prior Publication Data
US 2016/0123999 A1    May 5, 2016

(30) Foreign Application Priority Data
Jul. 9, 2013    (JP) ................................. 2013-143276

(51) Int. Cl.
*G01N 33/72* (2006.01)
*C12Q 1/26* (2006.01)
(52) U.S. Cl.
CPC ............. *G01N 33/723* (2013.01); *C12Q 1/26* (2013.01); *G01N 33/725* (2013.01)
(58) Field of Classification Search
None
See application file for complete search history.

(56) References Cited

U.S. PATENT DOCUMENTS

| | | | |
|---|---|---|---|
| 4,372,747 | A | 2/1983 | Gabbay et al. |
| 7,855,079 | B2 | 12/2010 | Yuan et al. |
| 8,304,249 | B2 | 11/2012 | Aisaka et al. |
| 8,318,501 | B2 | 11/2012 | Yuan et al. |
| 8,790,905 | B2 | 7/2014 | Aisaka et al. |
| 8,883,142 | B2 | 11/2014 | Aisaka et al. |
| RE46,118 | E | 8/2016 | Yonehara |
| RE46,130 | E | 8/2016 | Yonehara |
| 2003/0162242 | A1 | 8/2003 | Yonehara |
| 2008/0096230 | A1 | 4/2008 | Yuan et al. |
| 2008/0299597 | A1 | 12/2008 | Yuan et al. |
| 2011/0189712 | A1 | 8/2011 | Yuan et al. |
| 2011/0250627 | A1 | 10/2011 | Yuan et al. |
| 2012/0003678 | A1 | 1/2012 | Aisaka et al. |
| 2013/0078664 | A1 | 3/2013 | Yuan et al. |
| 2013/0098777 | A1 | 4/2013 | Gaustad |
| 2013/0171676 | A1 | 7/2013 | Murakami et al. |
| 2014/0057333 | A1 | 2/2014 | Aisaka et al. |

FOREIGN PATENT DOCUMENTS

| | | |
|---|---|---|
| CN | 101484809 A | 7/2009 |
| CN | 103124793 A | 5/2013 |
| EP | 1223224 A1 | 7/2002 |
| EP | 1291416 A1 | 3/2003 |
| EP | 1304385 A1 | 4/2003 |
| EP | 1555324 A1 | 7/2005 |
| EP | 1555325 A1 | 7/2005 |
| EP | 1626088 A1 | 2/2006 |
| EP | 2604698 A1 | 6/2013 |
| JP | 2001-095598 A | 4/2001 |
| JP | 2003-235585 A | 8/2003 |
| JP | 2009-544315 A | 12/2009 |
| WO | WO-2004/029613 A1 | 4/2004 |
| WO | WO-2004/038033 A1 | 5/2004 |
| WO | WO-2004/038034 A1 | 5/2004 |
| WO | WO-2004/104203 A1 | 12/2004 |
| WO | WO-2008/013874 A1 | 1/2008 |
| WO | WO-2008/108385 A1 | 9/2008 |
| WO | WO-2010/041715 A1 | 4/2010 |

OTHER PUBLICATIONS

International Search Report for International Patent Application No. PCT/JP2014/068010, dated Sep. 2, 2014 (English language translation provided) (6 pages).
Written Opinion of the International Searching Authority for International Patent Application No. PCT/JP2014/068010, dated Sep. 2, 2014 (English language translation provided) (8 pages).
International Preliminary Report on Patentability for International Patent Application No. PCT/JP2014/068010, dated Jan. 12, 2016 (English language translation provided) (10 pages).
Davis et al., "A high-performance liquid chromatography method for hemoglobin A1c," Diabetes. 27(2):102-7 (1978).
Finke et al., "Preparation of a candidate primary reference material for the international standardisation of HbA1c determinations," Clin Chem Lab Med. 36(5):299-308 (1998).
Hirokawa et al., "Enhancement of thermostability of fungal deglycating enzymes by directed evolution," Appl Microbiol Biotechnol. 78(5):775-81 (2008).
Katayama et al., "Tina-quant HbA1c, a homogenous immunoturbidimetric method for hemoglobin A1c," The Journal of the Japan Society for Clinical Laboratory Automation 18(4):620 (1993) (English language translation provided).

(Continued)

*Primary Examiner* — Suzanne M Noakes
*Assistant Examiner* — Stephen M Chong
(74) *Attorney, Agent, or Firm* — Clark & Elbing LLP

(57) ABSTRACT

The present invention provides a method for measuring glycated hemoglobin in a sample, which comprises directly oxidizing glycated hemoglobin in a sample, and then measuring a substance produced or consumed by the oxidation; and a method for measuring glycated hemoglobin in a sample, which comprises directly oxidizing glycated hemoglobin in a sample using an enzyme, and then measuring a substance produced or consumed by the oxidation. A method for measuring glycated hemoglobin of the present invention is useful for diagnosing lifestyle-related disease such as diabetes mellitus.

4 Claims, 4 Drawing Sheets

(56) References Cited

OTHER PUBLICATIONS

Extended European Search Report for European Patent Application No. 14823357.0 dated Dec. 8, 2016 (6 pages).

SEQUENCE LISTING

```
<160> NUMBER OF SEQ ID NOS: 108

<210> SEQ ID NO 1
<211> LENGTH: 438
<212> TYPE: PRT
<213> ORGANISM: Artificial
<220> FEATURE:
<223> OTHER INFORMATION: FPOX-15

<400> SEQUENCE: 1

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Arg Leu Arg Asn
    50                  55                  60

Lys Pro Asp Leu Gln Leu Tyr Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160
```

```
Ala Ala Lys Ala Ile Asn Ala Ile Gly Gln Phe Leu Lys Glu Gln Gly
            165                 170                 175

Val Lys Phe Gly Phe Gly Glu Ala Gly Thr Phe Lys Lys Pro Leu Phe
        180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
            405                 410                 415

Ser Arg Arg Ala Ala Pro Ala Lys Asp Leu Ala Asp Met Pro Gly Trp
        420                 425                 430

Arg Asn Glu Ala Lys Met
        435
```

<210> SEQ ID NO 2
<211> LENGTH: 438
<212> TYPE: PRT
<213> ORGANISM: Artificial
<220> FEATURE:
<223> OTHER INFORMATION: FPOX-9

<400> SEQUENCE: 2

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Met Ser Ile Arg Leu Arg Asn
    50                  55                  60

Lys Pro Asp Leu Gln Leu Tyr Leu Glu Ala Leu Asp Met Trp Lys Asn
65                  70                  75                  80
```

```
Asp Pro Leu Phe Lys Pro Phe His Asn Val Gly Gln Met Asp Val
                85                  90                  95

Ser Ser Thr Glu Glu Gly Ile Lys Gly Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Pro Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 3
<211> LENGTH: 438
<212> TYPE: PRT
<213> ORGANISM: Artificial
<220> FEATURE:
<223> OTHER INFORMATION: FPOX-18A

<400> SEQUENCE: 3
```

Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Cys Leu Glu Ala Leu Asp Met Trp Lys Asn
65                  70                  75                  80

Asp Pro Leu Phe Lys Pro Phe His Asn Val Gly Gln Met Asp Val
            85                  90                  95

Ser Ser Thr Glu Glu Gly Ile Lys Lys Leu Arg Met Arg Tyr Gln Ser
        100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 4
<211> LENGTH: 438
<212> TYPE: PRT
<213> ORGANISM: Artificial
<220> FEATURE:
<223> OTHER INFORMATION: FPOX-18B

<400> SEQUENCE: 4

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

```
Asn Asp Lys Glu Leu Phe Asn Arg Ala Met Cys Trp Cys Thr Asp Thr
                340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 5
<211> LENGTH: 438
<212> TYPE: PRT
<213> ORGANISM: Artificial
<220> FEATURE:
<223> OTHER INFORMATION: FPOX-18C

<400> SEQUENCE: 5

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asn Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255
```

-continued

```
Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 6
<211> LENGTH: 438
<212> TYPE: PRT
<213> ORGANISM: Artificial
<220> FEATURE:
<223> OTHER INFORMATION: FPOX-18D

<400> SEQUENCE: 6

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175
```

Val Lys Phe Gly Phe Gly Glu Ala Gly Thr Phe Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
            210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
            290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
            405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 7
<211> LENGTH: 438
<212> TYPE: PRT
<213> ORGANISM: Artificial
<220> FEATURE:
<223> OTHER INFORMATION: FPOX-19

<400> SEQUENCE: 7

```
Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 8
<211> LENGTH: 438
<212> TYPE: PRT
<213> ORGANISM: Artificial
<220> FEATURE:
<223> OTHER INFORMATION: FPOX-20

<400> SEQUENCE: 8

Met Ala Pro Arg Ala Asn Thr Lys Ile Ile Val Val Gly Gly Gly Gly
1               5                   10                  15
```

```
Thr Met Gly Ser Ser Thr Ala Leu His Leu Leu Arg Ala Gly Tyr Thr
         20                  25                  30

Pro Ser Asn Ile Thr Val Leu Asp Thr Tyr Pro Ile Pro Ser Ala Gln
         35                  40                  45

Ser Ala Gly Tyr Asp Leu Asn Lys Ile Phe Gly Ile Ser Gly Ala Asn
50                   55                  60

Lys Pro Asp Leu Gln Leu Ser Leu Glu Ala Ala Asp Met Trp Lys Asn
65                   70                  75                  80

Asp Pro Leu Phe Lys Pro Phe Phe His Asn Val Gly Gln Met Asp Val
             85                  90                  95

Ser Ser Thr Glu Glu Gly Ile Lys Lys Leu Arg Lys Arg Tyr Gln Ser
         100                 105                 110

Leu Leu Arg Ala Gly Ile Gly Leu Glu Lys Thr Asn Phe Leu Leu Glu
         115                 120                 125

Ser Glu Asp Glu Ile Leu Ala Lys Ala Pro His Phe Thr Arg Glu Gln
         130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                 165                 170                 175

Val Lys Phe Gly Phe Gly Glu Ala Gly Thr Phe Lys Lys Pro Leu Phe
             180                 185                 190

Ala Asp Ala Asp Glu Lys Thr Cys Ile Gly Val Glu Thr Val Asp Gly
             195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                 245                 250                 255

Thr Pro Val Ile Tyr Asp Gly Asp Tyr Gly Phe Phe Ile Glu Pro Asp
             260                 265                 270

Glu Asn Gly Ile Ile Lys Val Cys Asp Glu Phe Pro Gly Phe Thr His
         275                 280                 285

Phe Lys Met His Gln Pro Tyr Gly Ser Pro Val Pro Lys Leu Ile Ser
         290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                 325                 330                 335

Asn Asp Lys Glu Leu Phe Asn Arg Ala Met Cys Trp Cys Thr Asp Thr
             340                 345                 350

Ala Asp Ala Asn Leu Leu Val Cys Glu His Pro Arg Trp Lys Gly Phe
         355                 360                 365

Tyr Leu Ala Thr Gly Asp Ser Gly His Ser Phe Lys Leu Leu Pro Asn
         370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
             405                 410                 415

Ser Arg Arg Ala Ala Pro Ala Lys Asp Leu Ala Asp Met Pro Gly Trp
             420                 425                 430

Arg Asn Glu Ala Lys Met
```

-continued

435

<210> SEQ ID NO 9
<211> LENGTH: 438
<212> TYPE: PRT
<213> ORGANISM: Artificial
<220> FEATURE:
<223> OTHER INFORMATION: FPOX-21

<400> SEQUENCE: 9

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
```

```
                355                 360                 365
Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 10
<211> LENGTH: 438
<212> TYPE: PRT
<213> ORGANISM: Artificial
<220> FEATURE:
<223> OTHER INFORMATION: FPOX-22

<400> SEQUENCE: 10

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Thr Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
```

```
                275                 280                 285
Phe Lys Met His Gln Pro Tyr Gly Ser Pro Val Pro Lys Leu Ile Ser
290                 295                 300
Val Pro Arg Ser His Ala Lys His Pro Thr Asp Thr Tyr Pro His Ala
305                 310                 315                 320
Ser Glu Val Thr Ile Lys Lys Ala Ile Asn Arg Phe Leu Pro Arg Phe
                325                 330                 335
Asn Asp Lys Glu Leu Phe Asn Arg Ala Met Cys Trp Cys Thr Asp Thr
                340                 345                 350
Ala Asp Ala Asn Leu Leu Val Cys Glu His Pro Arg Trp Lys Gly Phe
                355                 360                 365
Tyr Leu Ala Thr Gly Asp Ser Gly His Ser Phe Lys Leu Leu Pro Asn
                370                 375                 380
Ile Gly Lys His Val Val Glu Leu Leu Glu Gly Arg Leu Glu Ser Val
385                 390                 395                 400
Phe Lys Asp Ala Trp Arg Trp Arg Pro Gly Ser Gly Asp Ala Leu Lys
                405                 410                 415
Ser Arg Arg Ala Ala Pro Ala Lys Asp Leu Ala Asp Met Pro Gly Trp
                420                 425                 430
Arg Asn Glu Ala Lys Met
                435

<210> SEQ ID NO 11
<211> LENGTH: 438
<212> TYPE: PRT
<213> ORGANISM: Artificial
<220> FEATURE:
<223> OTHER INFORMATION: FPOX-23

<400> SEQUENCE: 11

Met Ala Pro Arg Ala Asn Thr Lys Ile Ile Val Val Gly Gly Gly Gly
1               5                   10                  15
Thr Met Gly Ser Ser Thr Ala Leu His Leu Leu Arg Ala Gly Tyr Thr
                20                  25                  30
Pro Ser Asn Ile Thr Val Leu Asp Thr Tyr Pro Ile Pro Ser Ala Gln
                35                  40                  45
Ser Ala Gly His Asp Leu Asn Lys Ile Phe Gly Ile Ser Gly Ala Asn
                50                  55                  60
Lys Pro Asp Leu Gln Leu Ser Leu Glu Ala Phe Asp Met Trp Lys Asn
65                  70                  75                  80
Asp Pro Leu Phe Lys Pro Phe Phe His Asn Val Gly Gln Met Asp Val
                85                  90                  95
Ser Ser Thr Glu Glu Gly Ile Lys Lys Leu Arg Lys Arg Tyr Gln Ser
                100                 105                 110
Leu Leu Arg Ala Gly Ile Gly Leu Glu Lys Thr Asn Phe Leu Leu Glu
                115                 120                 125
Ser Glu Asp Glu Ile Leu Ala Lys Ala Pro His Phe Thr Arg Glu Gln
                130                 135                 140
Ile Lys Gly Trp Lys Gly Leu Phe Cys Gly Asp Gly Gly Trp Leu Ala
145                 150                 155                 160
Ala Ala Lys Ala Ile Asn Ala Ile Gly Gln Phe Leu Lys Glu Gln Gly
                165                 170                 175
Val Lys Phe Gly Phe Gly Glu Ala Gly Thr Phe Lys Lys Pro Leu Phe
                180                 185                 190
Ala Asp Ala Asp Glu Lys Thr Cys Ile Gly Val Glu Thr Val Asp Gly
```

```
            195                 200                 205
Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
                275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ala Asn Leu Leu Val Cys Glu His Pro Arg Trp Lys Gly Phe
                355                 360                 365

Tyr Leu Ala Thr Gly Asp Ser Gly His Ser Phe Lys Leu Leu Pro Asn
                370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
                435

<210> SEQ ID NO 12
<211> LENGTH: 438
<212> TYPE: PRT
<213> ORGANISM: Artificial
<220> FEATURE:
<223> OTHER INFORMATION: FPOX-24

<400> SEQUENCE: 12

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
                35                  40                  45

Ser Ala Gly Tyr Asp Leu Asn Lys Val Phe Gly Ile Ser Gly Ala Asn
            50                  55                  60

Lys Pro Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Lys Arg Tyr Gln Ser
                100                 105                 110

Leu Leu Arg Ala Gly Ile Gly Leu Glu Lys Thr Asn Phe Leu Leu Glu
```

```
            115                 120                 125
Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 13
<211> LENGTH: 438
<212> TYPE: PRT
<213> ORGANISM: Artificial
<220> FEATURE:
<223> OTHER INFORMATION: FPOX-25

<400> SEQUENCE: 13

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
```

```
            35                  40                  45
Ser Ala Gly Tyr Asp Leu Asn Lys Ile Phe Gly Ile Ser Gly Ala Asn
 50                  55                  60

Lys His Asp Leu Gln Leu Ser Leu Glu Ala Phe Asp Met Trp Lys Asn
 65                  70                  75                  80

Asp Pro Leu Phe Lys Pro Phe Phe His Asn Val Gly Gln Met Asp Val
                 85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 14
```

<211> LENGTH: 438
<212> TYPE: PRT
<213> ORGANISM: Artificial
<220> FEATURE:
<223> OTHER INFORMATION: FPOX-26

<400> SEQUENCE: 14

Met Ala Pro Arg Ala Asn Thr Lys Ile Ile Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu

```
Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
            405                 410                 415

Ser Arg Arg Ala Ala Pro Ala Lys Asp Leu Ala Asp Met Pro Gly Trp
        420                 425                 430

Arg Asn Glu Ala Lys Met
        435

<210> SEQ ID NO 15
<211> LENGTH: 438
<212> TYPE: PRT
<213> ORGANISM: Artificial
<220> FEATURE:
<223> OTHER INFORMATION: FPOX-27

<400> SEQUENCE: 15

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys Pro Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Arg Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300
```

-continued

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 16
<211> LENGTH: 438
<212> TYPE: PRT
<213> ORGANISM: Artificial
<220> FEATURE:
<223> OTHER INFORMATION: FPOX-28

<400> SEQUENCE: 16

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys Pro Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

```
Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
            290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 17
<211> LENGTH: 438
<212> TYPE: PRT
<213> ORGANISM: Artificial
<220> FEATURE:
<223> OTHER INFORMATION: FPOX-29

<400> SEQUENCE: 17

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys Pro Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140
```

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
            165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
                195                 200                 205

Thr Lys Tyr Tyr Ala Asp Lys Val Val Leu Ala Ala Gly Ala Trp Ser
        210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
        435

<210> SEQ ID NO 18
<211> LENGTH: 438
<212> TYPE: PRT
<213> ORGANISM: Artificial
<220> FEATURE:
<223> OTHER INFORMATION: FPOX-30

<400> SEQUENCE: 18

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Glu Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 19
<211> LENGTH: 438
<212> TYPE: PRT
<213> ORGANISM: Artificial
<220> FEATURE:

<223> OTHER INFORMATION: FPOX-31

<400> SEQUENCE: 19

```
Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Glu Val
                85                  90                  95

Ser Ser Thr Glu Glu Gly Ile Lys Arg Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400
```

```
Phe Lys Asp Ala Trp Arg Trp Arg Pro Gly Ser Gly Asp Ala Leu Lys
                405                 410                 415
Ser Arg Arg Ala Ala Pro Ala Lys Asp Leu Ala Asp Met Pro Gly Trp
            420                 425                 430
Arg Asn Glu Ala Lys Met
        435
```

<210> SEQ ID NO 20
<211> LENGTH: 438
<212> TYPE: PRT
<213> ORGANISM: Artificial
<220> FEATURE:
<223> OTHER INFORMATION: FPOX-32

<400> SEQUENCE: 20

```
Met Ala Pro Arg Ala Asn Thr Lys Ile Ile Val Val Gly Gly Gly Gly
1               5                   10                  15
Thr Met Gly Ser Ser Thr Ala Leu His Leu Leu Arg Ala Gly Tyr Thr
            20                  25                  30
Pro Ser Asn Ile Thr Val Leu Asp Thr Tyr Pro Ile Pro Ser Ala Gln
        35                  40                  45
Ser Ala Gly Tyr Asp Leu Asn Lys Ile Phe Gly Ile Ser Gly Ala Asn
    50                  55                  60
Lys His Asp Leu Gln Leu Ser Leu Glu Ala Phe Asp Met Trp Lys Asn
65                  70                  75                  80
Asp Pro Leu Phe Lys Pro Phe His Asn Val Gly Gln Met Glu Val
                85                  90                  95
Ser Ser Thr Glu Glu Gly Ile Lys Arg Leu Arg Arg Tyr Gln Ser
            100                 105                 110
Leu Leu Arg Ala Gly Ile Gly Leu Glu Lys Thr Asn Phe Leu Leu Glu
        115                 120                 125
Ser Glu Asp Glu Ile Leu Ala Lys Ala Pro His Phe Thr Arg Glu Gln
    130                 135                 140
Ile Lys Gly Trp Lys Gly Leu Phe Cys Gly Asp Gly Gly Trp Leu Ala
145                 150                 155                 160
Ala Ala Lys Ala Ile Asn Ala Ile Gly Gln Phe Leu Lys Glu Gln Gly
                165                 170                 175
Val Lys Phe Gly Phe Gly Glu Ala Gly Thr Phe Lys Lys Pro Leu Phe
            180                 185                 190
Ala Asp Ala Asp Glu Lys Thr Cys Ile Gly Val Glu Thr Val Asp Gly
        195                 200                 205
Thr Lys Tyr Tyr Ala Asp Lys Val Val Leu Ala Ala Gly Ala Trp Ser
    210                 215                 220
Ser Thr Leu Val Asp Leu Glu Glu Gln Cys Val Ser Lys Ala Trp Val
225                 230                 235                 240
Phe Ala His Ile Gln Leu Thr Pro Ala Glu Ala Ala Tyr Lys Asn
                245                 250                 255
Thr Pro Val Ile Tyr Asp Gly Asp Tyr Gly Phe Ile Glu Pro Asp
            260                 265                 270
Glu Asn Gly Ile Ile Lys Val Cys Asp Glu Phe Pro Gly Phe Thr His
        275                 280                 285
Phe Lys Met His Gln Pro Tyr Gly Ser Pro Val Pro Lys Leu Ile Ser
    290                 295                 300
Val Pro Arg Ser His Ala Lys His Pro Thr Asp Thr Tyr Pro His Ala
305                 310                 315                 320
```

```
Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
        340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 21
<211> LENGTH: 438
<212> TYPE: PRT
<213> ORGANISM: Artificial
<220> FEATURE:
<223> OTHER INFORMATION: FPOX-33

<400> SEQUENCE: 21

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Thr Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Glu Val
                85                  90                  95

Ser Ser Thr Glu Glu Gly Ile Lys Arg Leu Arg Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240
```

-continued

```
Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
        260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435
```

<210> SEQ ID NO 22
<211> LENGTH: 438
<212> TYPE: PRT
<213> ORGANISM: Artificial
<220> FEATURE:
<223> OTHER INFORMATION: FPOX-34

<400> SEQUENCE: 22

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly His Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Glu Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160
```

```
Ala Ala Lys Ala Ile Asn Ala Ile Gly Gln Phe Leu Lys Glu Gln Gly
            165                 170                 175

Val Lys Phe Gly Phe Gly Glu Ala Gly Thr Phe Lys Lys Pro Leu Phe
        180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
        260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
        340                 345                 350

Ala Asp Ala Asn Leu Leu Val Cys Glu His Pro Arg Trp Lys Gly Phe
    355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
        420                 425                 430

Arg Asn Glu Ala Lys Met
        435
```

<210> SEQ ID NO 23
<211> LENGTH: 438
<212> TYPE: PRT
<213> ORGANISM: Artificial
<220> FEATURE:
<223> OTHER INFORMATION: FPOX-35

<400> SEQUENCE: 23

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Val Phe Gly Ile Ser Gly Ala Asn
    50                  55                  60

Lys His Asp Leu Gln Leu Ser Leu Glu Ala Phe Asp Met Trp Lys Asn
65                  70                  75                  80
```

Asp Pro Leu Phe Lys Pro Phe Phe His Asn Val Gly Gln Met Glu Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
            130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 24
<211> LENGTH: 438
<212> TYPE: PRT
<213> ORGANISM: Artificial
<220> FEATURE:
<223> OTHER INFORMATION: FPOX-36

<400> SEQUENCE: 24

```
Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
```

Arg Asn Glu Ala Lys Met
                435

<210> SEQ ID NO 25
<211> LENGTH: 438
<212> TYPE: PRT
<213> ORGANISM: Artificial
<220> FEATURE:
<223> OTHER INFORMATION: FPOX-37

<400> SEQUENCE: 25

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr

```
              340                 345                 350
Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 26
<211> LENGTH: 438
<212> TYPE: PRT
<213> ORGANISM: Artificial
<220> FEATURE:
<223> OTHER INFORMATION: FPOX-38

<400> SEQUENCE: 26

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
```

```
                260                 265                 270
Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 27
<211> LENGTH: 438
<212> TYPE: PRT
<213> ORGANISM: Artificial
<220> FEATURE:
<223> OTHER INFORMATION: FPOX-39

<400> SEQUENCE: 27

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Glu Val
                85                  90                  95

Ser Ser Thr Glu Glu Gly Ile Lys Lys Leu Arg Lys Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
```

```
                180             185             190
Ala Asp Ala Asp Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
        210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ser Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 28
<211> LENGTH: 438
<212> TYPE: PRT
<213> ORGANISM: Artificial
<220> FEATURE:
<223> OTHER INFORMATION: FPOX-40

<400> SEQUENCE: 28

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Arg Leu Arg Lys Arg Tyr Gln Ser
```

```
            100                 105                 110
Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 29
<211> LENGTH: 438
<212> TYPE: PRT
<213> ORGANISM: Artificial
<220> FEATURE:
<223> OTHER INFORMATION: FPOX-41

<400> SEQUENCE: 29

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
```

-continued

Pro Ser Asn Ile Thr Val Leu Asp Thr Tyr Pro Ile Pro Ser Ala Gln
            20                  25                  30
Ser Ala Gly Tyr Asp Leu Asn Lys Ile Phe Gly Ile Ser Gly Ala Asn
        35                  40                  45
Lys His Asp Leu Gln Leu Ser Leu Glu Ala Phe Asp Met Trp Lys Asn
 50                  55                  60
 65                  70                  75                  80
Asp Pro Leu Phe Lys Pro Phe His Asn Val Gly Gln Met Asp Val
                    85                  90                  95
Ser Ser Thr Glu Glu Gly Ile Lys Lys Leu Arg Arg Arg Tyr Gln Ser
                100                 105                 110
Leu Leu Arg Ala Gly Ile Gly Leu Glu Lys Thr Asn Phe Leu Leu Glu
            115                 120                 125
Ser Glu Asp Glu Ile Leu Ala Lys Ala Pro His Phe Thr Arg Glu Gln
        130                 135                 140
Ile Lys Gly Trp Lys Gly Leu Phe Cys Gly Asp Gly Gly Trp Leu Ala
145                 150                 155                 160
Ala Ala Lys Ala Ile Asn Ala Ile Gly Gln Phe Leu Lys Glu Gln Gly
                165                 170                 175
Val Lys Phe Gly Phe Gly Glu Ala Gly Thr Phe Lys Lys Pro Leu Phe
            180                 185                 190
Ala Asp Ala Asp Glu Lys Thr Cys Ile Gly Val Glu Thr Val Asp Gly
        195                 200                 205
Thr Lys Tyr Tyr Ala Asp Lys Val Leu Ala Ala Gly Ala Trp Ser
    210                 215                 220
Ser Thr Leu Val Asp Leu Glu Glu Gln Cys Val Ser Lys Ala Trp Val
225                 230                 235                 240
Phe Ala His Ile Gln Leu Thr Pro Ala Glu Ala Ala Tyr Lys Asn
                245                 250                 255
Thr Pro Val Ile Tyr Asp Gly Asp Tyr Gly Phe Phe Ile Glu Pro Asp
            260                 265                 270
Glu Asn Gly Ile Ile Lys Val Cys Asp Glu Phe Pro Gly Phe Thr His
        275                 280                 285
Phe Lys Met His Gln Pro Tyr Gly Ser Pro Val Pro Lys Leu Ile Ser
    290                 295                 300
Val Pro Arg Ser His Ala Lys His Pro Thr Asp Thr Tyr Pro His Ala
305                 310                 315                 320
Ser Glu Val Thr Ile Lys Lys Ala Ile Asn Arg Phe Leu Pro Arg Phe
                325                 330                 335
Asn Asp Lys Glu Leu Phe Asn Arg Ala Met Cys Trp Cys Thr Asp Thr
            340                 345                 350
Ala Asp Ser Asn Leu Leu Val Cys Glu His Pro Arg Trp Lys Gly Phe
        355                 360                 365
Tyr Leu Ala Thr Gly Asp Ser Gly His Ser Phe Lys Leu Leu Pro Asn
    370                 375                 380
Ile Gly Lys His Val Val Glu Leu Leu Glu Gly Arg Leu Glu Ser Val
385                 390                 395                 400
Phe Lys Asp Ala Trp Arg Trp Arg Pro Gly Ser Gly Asp Ala Leu Lys
                405                 410                 415
Ser Arg Arg Ala Ala Pro Ala Lys Asp Leu Ala Asp Met Pro Gly Trp
            420                 425                 430
Arg Asn Glu Ala Lys Met
            435

<210> SEQ ID NO 30
<211> LENGTH: 438
<212> TYPE: PRT
<213> ORGANISM: Artificial
<220> FEATURE:
<223> OTHER INFORMATION: FPOX-42

<400> SEQUENCE: 30

```
Met Ala Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
            195                 200                 205

Thr Lys Tyr Tyr Ala Asp Lys Val Leu Ala Ala Gly Ala Trp Ser
        210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365
```

Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 31
<211> LENGTH: 438
<212> TYPE: PRT
<213> ORGANISM: Artificial
<220> FEATURE:
<223> OTHER INFORMATION: FPOX-43

<400> SEQUENCE: 31

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Thr Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

```
Phe Lys Met His Gln Pro Tyr Gly Ser Pro Val Pro Lys Leu Ile Ser
        290                 295                 300
Val Pro Arg Ser His Ala Lys His Pro Thr Asp Thr Tyr Pro His Ala
305                 310                 315                 320
Ser Glu Val Thr Ile Lys Lys Ala Ile Asn Arg Phe Leu Pro Arg Phe
                325                 330                 335
Asn Asp Lys Glu Leu Phe Asn Arg Ala Met Cys Trp Cys Thr Asp Thr
            340                 345                 350
Ala Asp Ser Asn Leu Leu Val Cys Glu His Pro Arg Trp Lys Gly Phe
        355                 360                 365
Tyr Leu Ala Thr Gly Asp Ser Gly His Ser Phe Lys Leu Leu Pro Asn
    370                 375                 380
Ile Gly Lys His Val Val Glu Leu Leu Glu Gly Arg Leu Glu Ser Val
385                 390                 395                 400
Phe Lys Asp Ala Trp Arg Trp Arg Pro Gly Ser Gly Asp Ala Leu Lys
                405                 410                 415
Ser Arg Arg Ala Ala Pro Ala Lys Asp Leu Ala Asp Met Pro Gly Trp
            420                 425                 430
Arg Asn Glu Ala Lys Met
        435

<210> SEQ ID NO 32
<211> LENGTH: 438
<212> TYPE: PRT
<213> ORGANISM: Artificial
<220> FEATURE:
<223> OTHER INFORMATION: FPOX-44

<400> SEQUENCE: 32

Met Ala Pro Arg Ala Asn Thr Lys Ile Ile Val Val Gly Gly Gly Gly
1               5                   10                  15
Thr Met Gly Ser Ser Thr Ala Leu His Leu Leu Arg Ala Gly Tyr Thr
                20                  25                  30
Pro Ser Asn Ile Thr Val Leu Asp Thr Tyr Pro Ile Pro Ser Ala Gln
            35                  40                  45
Ser Ala Gly His Asp Leu Asn Lys Ile Phe Gly Ile Ser Gly Ala Asn
        50                  55                  60
Lys His Asp Leu Gln Leu Ser Leu Glu Ala Phe Asp Met Trp Lys Asn
65                  70                  75                  80
Asp Pro Leu Phe Lys Pro Phe Phe His Asn Val Gly Gln Met Asp Val
                85                  90                  95
Ser Ser Thr Glu Glu Gly Ile Lys Arg Leu Arg Arg Arg Tyr Gln Ser
            100                 105                 110
Leu Leu Arg Ala Gly Ile Gly Leu Glu Lys Thr Asn Phe Leu Leu Glu
        115                 120                 125
Ser Glu Asp Glu Ile Leu Ala Lys Ala Pro His Phe Thr Arg Glu Gln
    130                 135                 140
Ile Lys Gly Trp Lys Gly Leu Phe Cys Gly Asp Gly Gly Trp Leu Ala
145                 150                 155                 160
Ala Ala Lys Ala Ile Asn Ala Ile Gly Gln Phe Leu Lys Glu Gln Gly
                165                 170                 175
Val Lys Phe Gly Phe Gly Glu Ala Gly Thr Phe Lys Lys Pro Leu Phe
            180                 185                 190
Ala Asp Ala Asp Glu Lys Thr Cys Ile Gly Val Glu Thr Val Asp Gly
        195                 200                 205
```

Thr Lys Tyr Tyr Ala Asp Lys Val Val Leu Ala Ala Gly Ala Trp Ser
                210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
                275                 280                 285

Phe Lys Met His Gln Pro Tyr Gly Ser Pro Val Pro Lys Leu Ile Ser
                290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ser Asn Leu Leu Val Cys Glu His Pro Arg Trp Lys Gly Phe
                355                 360                 365

Tyr Leu Ala Thr Gly Asp Ser Gly His Ser Phe Lys Leu Leu Pro Asn
                370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
                435

<210> SEQ ID NO 33
<211> LENGTH: 438
<212> TYPE: PRT
<213> ORGANISM: Artificial
<220> FEATURE:
<223> OTHER INFORMATION: FPOX-45

<400> SEQUENCE: 33

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
                35                  40                  45

Ser Ala Gly Tyr Asp Leu Asn Lys Val Phe Gly Ile Ser Gly Ala Asn
                50                  55                  60

Lys His Asp Leu Gln Leu Ser Leu Glu Ala Phe Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Arg Leu Arg Arg Tyr Gln Ser
                100                 105                 110

Leu Leu Arg Ala Gly Ile Gly Leu Glu Lys Thr Asn Phe Leu Leu Glu
                115                 120                 125

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
                180                 185                 190

Ala Asp Ala Asp Glu Lys Thr Cys Ile Gly Val Glu Thr Val Asp Gly
                195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
                275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
                340                 345                 350

Ala Asp Ser Asn Leu Leu Val Cys Glu His Pro Arg Trp Lys Gly Phe
                355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
                435

<210> SEQ ID NO 34
<211> LENGTH: 438
<212> TYPE: PRT
<213> ORGANISM: Artificial
<220> FEATURE:
<223> OTHER INFORMATION: FPOX-46

<400> SEQUENCE: 34

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
                35                  40                  45

Ser Ala Gly Tyr Asp Leu Asn Lys Ile Phe Gly Ile Ser Gly Ala Asn
        50                  55                  60

Lys His Asp Leu Gln Leu Ser Leu Glu Ala Phe Asp Met Trp Lys Asn
 65                  70                  75                  80

Asp Pro Leu Phe Lys Pro Phe His Asn Val Gly Gln Met Glu Val
                85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 35
<211> LENGTH: 1317

<212> TYPE: DNA
<213> ORGANISM: Artificial
<220> FEATURE:
<223> OTHER INFORMATION: FPOX-15

<400> SEQUENCE: 35

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaaaat cttcggcatc     180
aggctgcgca acaagcctga cttacaactc tatcttgagg cgctggacat gtggaaaaat     240
gatcctctat tcaagccgtt tttccacaat gttggacaga tggacgtctc ttcaacagaa     300
gaaggcatca aaaagcttcg catgagatac cagtctcttc tcgacgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600
atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga tgaggcaaa gatgtag       1317
```

<210> SEQ ID NO 36
<211> LENGTH: 1317
<212> TYPE: DNA
<213> ORGANISM: Artificial
<220> FEATURE:
<223> OTHER INFORMATION: FPOX-9

<400> SEQUENCE: 36

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaaaat catgagcatc     180
aggctgcgca acaagcctga cttacaactc tatcttgagg cgctggacat gtggaaaaat     240
gatcctctat tcaagccgtt tttccacaat gttggacaga tggacgtctc ttcaacagaa     300
gaaggcatca aaggtcttcg catgagatac cagtctcttc tcgacgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
```

```
tttggcggcg ccggcacgtt caaaaagcca ctcttcgccg atgccgacga gaagacgtgc    600
atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccgaatgaga acggcatcat aaaagtctgc    840
gacgaattcc ctggcttcac gcacttcaag atgcaccagc cgtacggctc accggtgccc    900
aaaccaatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga tgaggcaaa gatgtag       1317
```

<210> SEQ ID NO 37
<211> LENGTH: 1317
<212> TYPE: DNA
<213> ORGANISM: Artificial
<220> FEATURE:
<223> OTHER INFORMATION: FPOX-18A

<400> SEQUENCE: 37

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga acaagcctga cttacaactc tgccttgagg cgctggacat gtggaaaaat    240
gatcctctat tcaagccgtt tttccacaat gttggacaga tggacgtctc ttcaacagaa    300
gaaggcatca aaaagcttcg catgagatac cagtctcttc tcgacgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga gaagacgtgc    600
atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga tgaggcaaa gatgtag       1317
```

<210> SEQ ID NO 38
<211> LENGTH: 1317
<212> TYPE: DNA
<213> ORGANISM: Artificial
<220> FEATURE:
<223> OTHER INFORMATION: FPOX-18B

<400> SEQUENCE: 38

| | | | | | |
|---|---|---|---|---|---|
| atggcgcccc | gagccaacac | caaaatcatc | gtcgtcggcg | gcggcggcac | aatgggctcg | 60 |
| tcgacagccc | tacacctcct | gcgcgccggc | tacacgccgt | ccaacatcac | agtgctcgac | 120 |
| acgtacccta | tcccttccgc | acagtctgca | ggctacgacc | tgaacaagat | cttcggcatc | 180 |
| tcaggcgcga | acaagcctga | cttacaactc | agccttgagg | cgctggacat | gtggaaaaat | 240 |
| gatcctctat | tcaagccgtt | tttccacaat | gttggacaga | tggacgtctc | ttcaacagaa | 300 |
| gaaggcatca | aaaagcttcg | catgagatac | cagtctcttc | tcgacgcagg | cattgggctc | 360 |
| gagaagacga | atttcctgct | ggaaagtgaa | gacgagatcc | tggctaaagc | gccgcatttc | 420 |
| acgcgggagc | agattaaagg | ctggaaaggg | ctgttctgtg | gcgacggcgg | ttggctcgct | 480 |
| gcagccaaag | ccatcaatgc | catcgggcag | ttcctcaagg | aacagggcgt | caagtttgga | 540 |
| tttggcgagg | ccggcacgtt | caaaaagcca | ctcttcgccg | atgccgacga | aagacgtgc | 600 |
| atcggcgtcg | aaactgtaga | cggcacaaaa | tactacgccg | acaaggtcgt | tctagcagct | 660 |
| ggtgcctgga | gttcgacgtt | ggtcgatctg | gaggagcagt | gcgtttcaaa | ggcctgggtc | 720 |
| tttgcccaca | tccaactgac | gcccgctgaa | gcagccgcgt | acaagaacac | tcctgttata | 780 |
| tacgacggtg | actatgggtt | tttcattgag | ccggacgaga | acggcatcat | aaaagtctgc | 840 |
| gacgaattcc | ctggcttcac | gcacttcaag | atgcaccagc | cgtacggctc | accggtgccc | 900 |
| aaattgatct | ctgtgcctcg | ctcccatgcg | aagcacccca | cagatacata | cccgcacgcg | 960 |
| tcggaggtca | ccatcaaaaa | ggctatcaac | cggttcctgc | cgaggttcaa | tgacaaggaa | 1020 |
| ctgtttaaca | gggccatgtg | ctggtgcacc | gataccgcgg | atgcaaatct | gcttgtttgt | 1080 |
| gagcatccac | gctggaaggg | gttttatctt | gcaacagggg | acagcgggca | ttcgttcaag | 1140 |
| ttgctgccga | atattggaaa | gcacgttgtc | gagttattgg | aggggaggct | ggaaagtgtg | 1200 |
| tttaaggatg | cttggaggtg | gaggcctggc | agtgggatg | cattaaagag | tagacgggct | 1260 |
| gcgcctgcga | aggacctggc | ggatatgccg | gggtggagga | tgaggcaaa | gatgtag | 1317 |

<210> SEQ ID NO 39
<211> LENGTH: 1317
<212> TYPE: DNA
<213> ORGANISM: Artificial
<220> FEATURE:
<223> OTHER INFORMATION: FPOX-18C

<400> SEQUENCE: 39

| | | | | | |
|---|---|---|---|---|---|
| atggcgcccc | gagccaacac | caaaatcatc | gtcgtcggcg | gcggcggcac | aatgggctcg | 60 |
| tcgacagccc | tacacctcct | gcgcgccggc | tacacgccgt | ccaacatcac | agtgctcgac | 120 |
| acgtacccta | tcccttccgc | acagtctgca | ggctacgacc | tgaacaagat | cttcggcatc | 180 |
| tcaggcgcga | acaagcctga | cttacaactc | agccttgagg | cgctggacat | gtggaaaaat | 240 |
| gatcctctat | tcaagccgtt | tttccacaat | gttggacaga | tggacgtctc | ttcaacagaa | 300 |
| gaaggcatca | aaaagcttcg | catgagatac | cagtctcttc | tcaacgcagg | cattgggctc | 360 |
| gagaagacga | atttcctgct | ggaaagtgaa | gacgagatcc | tggctaaagc | gccgcatttc | 420 |

```
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga tgaggcaaa gatgtag       1317
```

<210> SEQ ID NO 40
<211> LENGTH: 1317
<212> TYPE: DNA
<213> ORGANISM: Artificial
<220> FEATURE:
<223> OTHER INFORMATION: FPOX-18D

<400> SEQUENCE: 40

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga acaagcctga cttacaactc agccttgagg cgctggacat gtggaaaaat    240
gatcctctat tcaagccgtt tttccacaat gttggacaga tggacgtctc ttcaacagaa    300
gaaggcatca aaaagcttcg catgagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
```

```
tttaaggatg cttggaggtg gaggcctggc agtggggatg cattaaagag tagacgggct    1260
gcgcctgcga aggacctggc ggatatgccg gggtggagga atgaggcaaa gatgtag       1317
```

<210> SEQ ID NO 41
<211> LENGTH: 1317
<212> TYPE: DNA
<213> ORGANISM: Artificial
<220> FEATURE:
<223> OTHER INFORMATION: FPOX-19

<400> SEQUENCE: 41

```
atggcgcccc gagccaacac caaaatcatc gtcgtcggcg gcggcggcac aatgggctcg    60
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga acaagcctga cttacaactc agccttgagg cgctggacat gtggaaaaat    240
gatcctctat tcaagccgtt tttccacaat gttggacaga tggacgtctc ttcaacagaa    300
gaaggcatca aaaagcttcg caaaagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga atgaggcaaa gatgtag       1317
```

<210> SEQ ID NO 42
<211> LENGTH: 1317
<212> TYPE: DNA
<213> ORGANISM: Artificial
<220> FEATURE:
<223> OTHER INFORMATION: FPOX-20

<400> SEQUENCE: 42

```
atggcgcccc gagccaacac caaaatcatc gtcgtcggcg gcggcggcac aatgggctcg    60
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga acaagcctga cttacaactc agccttgagg cggccgacat gtggaaaaat    240
gatcctctat tcaagccgtt tttccacaat gttggacaga tggacgtctc ttcaacagaa    300
```

| | |
|---|---|
| gaaggcatca aaaagcttcg caaaagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtgggatg cattaaagag tagacgggct | 1260 |
| gcgcctgcga aggacctggc ggatatgccg gggtggagga tgaggcaaa gatgtag | 1317 |

<210> SEQ ID NO 43
<211> LENGTH: 1317
<212> TYPE: DNA
<213> ORGANISM: Artificial
<220> FEATURE:
<223> OTHER INFORMATION: FPOX-21

<400> SEQUENCE: 43

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggctacgacc tgaacaagat cttcggcatc | 180 |
| tcaggcgcga acaagcctga cttacaactc tcgcttgagg cgttcgacat gtggaaaaat | 240 |
| gatcctctat tcaagccgtt ttttccacaat gttggacaga tggacgtctc ttcaacagaa | 300 |
| gaaggcatca aaagcttcg caaaagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |

```
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtgggatg cattaaagag tagacgggct     1260
gcgcctgcga aggacctggc ggatatgccg gggtggagga atgaggcaaa gatgtag       1317
```

<210> SEQ ID NO 44
<211> LENGTH: 1317
<212> TYPE: DNA
<213> ORGANISM: Artificial
<220> FEATURE:
<223> OTHER INFORMATION: FPOX-22

<400> SEQUENCE: 44

```
atggcgcccc gagccaacac caaaatcatc gtcgtcggcg gcggcggcac aatgggctcg    60
tcgacagccc tacacctcct gcgcgccggc tacacgccga ccaacatcac agtgctcgac    120
acgtacccta tcccttccgc acagtctgca ggctacgacc tgaacaagat cttcggcatc    180
tcaggcgcga acaagcctga cttacaactc tcgcttgagg cgttcgacat gtggaaaaat    240
gatcctctat tcaagccgtt tttccacaat gttggacaga tggacgtctc ttcaacagaa    300
gaaggcatca aaaagcttcg caaaagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgtttata   780 tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgttgtt   1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtgggatg cattaaagag tagacgggct     1260
gcgcctgcga aggacctggc ggatatgccg gggtggagga atgaggcaaa gatgtag       1317
```

<210> SEQ ID NO 45
<211> LENGTH: 1317
<212> TYPE: DNA
<213> ORGANISM: Artificial
<220> FEATURE:
<223> OTHER INFORMATION: FPOX-23

<400> SEQUENCE: 45

```
atggcgcccc gagccaacac caaaatcatc gtcgtcggcg gcggcggcac aatgggctcg    60
tcgacagccc tacacctcct gcgcgccggc tacacgccgt ccaacatcac agtgctcgac    120
acgtacccta tcccttccgc acagtctgca ggccatgacc tgaacaagat cttcggcatc    180
```

```
tcaggcgcga acaagcctga cttacaactc tcgcttgagg cgttcgacat gtggaaaaat    240
gatcctctat tcaagccgtt tttccacaat gttggacaga tggacgtctc ttcaacagaa    300
gaaggcatca aaaagcttcg caaaagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtgggatgc attaaagag tagacgggct    1260 gcgcctgcga aggacctggc ggatatgccg gggtggagga atgaggcaaa gatgtag      1317
```

<210> SEQ ID NO 46
<211> LENGTH: 1317
<212> TYPE: DNA
<213> ORGANISM: Artificial
<220> FEATURE:
<223> OTHER INFORMATION: FPOX-24

<400> SEQUENCE: 46

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggctacgacc tgaacaaggt cttcggcatc    180
tcaggcgcga acaagcctga cttacaactc tcgcttgagg cgttcgacat gtggaaaaat    240
gatcctctat tcaagccgtt tttccacaat gttggacaga tggacgtctc ttcaacagaa    300
gaaggcatca aaaagcttcg caaaagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
```

-continued

| | |
|---|---|
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 47
<211> LENGTH: 1317
<212> TYPE: DNA
<213> ORGANISM: Artificial
<220> FEATURE:
<223> OTHER INFORMATION: FPOX-25

<400> SEQUENCE: 47

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggctacgacc tgaacaagat cttcggcatc | 180 |
| tcaggcgcga acaagcatga cttacaactc tcgcttgagg cgttcgacat gtggaaaaat | 240 |
| gatcctctat tcaagccgtt tttccacaat gttggacaga tggacgtctc ttcaacagaa | 300 |
| gaaggcatca aaaagcttcg caaaagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaagggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atgcaaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 48
<211> LENGTH: 1317
<212> TYPE: DNA
<213> ORGANISM: Artificial
<220> FEATURE:
<223> OTHER INFORMATION: FPOX-26

<400> SEQUENCE: 48

| | |
|---|---|
| atggcgcccc gagccaacac caaaatcatc gtcgtcggcg gcggcggcac aatgggctcg | 60 |

```
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcctga cttacaactc tcgcttgagg cgttcgacat gtggaaaaat     240
gatcctctat tcaagccgtt tttccacaat gttggacaga tggaagtctc ttcaacagaa     300
gaaggcatca aaaagcttcg caaaagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600 atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga atgaggcaaa gatgtag       1317
```

<210> SEQ ID NO 49
<211> LENGTH: 1317
<212> TYPE: DNA
<213> ORGANISM: Artificial
<220> FEATURE:
<223> OTHER INFORMATION: FPOX-27

<400> SEQUENCE: 49

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcctga cttacaactc tcgcttgagg cgttcgacat gtggaaaaat     240
gatcctctat tcaagccgtt tttccacaat gttggacaga tggacgtctc ttcaacagaa     300
gaaggcatca aacgccttcg caaaagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600 atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
```

```
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 50
<211> LENGTH: 1317
<212> TYPE: DNA
<213> ORGANISM: Artificial
<220> FEATURE:
<223> OTHER INFORMATION: FPOX-28

<400> SEQUENCE: 50

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga acaagcctga cttacaactc tcgcttgagg cgttcgacat gtggaaaaat    240
gatcctctat tcaagccgtt tttccacaat gttggacaga tggacgtctc ttcaacagaa    300
gaaggcatca aaaagcttcg ccgcagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga agacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 51
<211> LENGTH: 1317
<212> TYPE: DNA
<213> ORGANISM: Artificial
<220> FEATURE:
<223> OTHER INFORMATION: FPOX-29

```
<400> SEQUENCE: 51
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcctga cttacaactc tcgcttgagg cgttcgacat gtggaaaaat     240
gatcctctat tcaagccgtt tttccacaat gttggacaga tggacgtctc ttcaacagaa     300
gaaggcatca aaaagcttcg caaaagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600 atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atagcaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga tgaggcaaa gatgtag        1317

<210> SEQ ID NO 52
<211> LENGTH: 1317
<212> TYPE: DNA
<213> ORGANISM: Artificial
<220> FEATURE:
<223> OTHER INFORMATION: FPOX-30

<400> SEQUENCE: 52
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcatga cttacaactc tcgcttgagg cgttcgacat gtggaaaaat     240
gatcctctat tcaagccgtt tttccacaat gttggacaga tggaagtctc ttcaacagaa     300
gaaggcatca aaaagcttcg caaaagatac cagtctcttc tccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600 atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
```

```
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 53
<211> LENGTH: 1317
<212> TYPE: DNA
<213> ORGANISM: Artificial
<220> FEATURE:
<223> OTHER INFORMATION: FPOX-31

<400> SEQUENCE: 53

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga acaagcatga cttacaactc tcgcttgagg cgttcgacat gtggaaaaat    240
gatcctctat tcaagccgtt tttccacaat gttggacaga tggaagtctc ttcaacagaa    300
gaaggcatca aacgccttcg caaaagatac cagtctcttc ccgcgcagg cattgggctc     360 gagaagacga atttcctgct ggaaagtgaa gacgagatcc tggctaaagc gccgcatttc    420
acgcgggagc agattaaagg ctggaagggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga agagacgtgc    600
atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 54
<211> LENGTH: 1317
<212> TYPE: DNA

<213> ORGANISM: Artificial
<220> FEATURE:
<223> OTHER INFORMATION: FPOX-32

<400> SEQUENCE: 54

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcatga cttacaactc tcgcttgagg cgttcgacat gtggaaaaat     240
gatcctctat tcaagccgtt tttccacaat gttggacaga tggaagtctc ttcaacagaa     300
gaaggcatca aacgccttcg ccgcagatac cagtctcttc ccgcgcagg cattgggctc      360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600
atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga atgaggcaaa gatgtag      1317
```

<210> SEQ ID NO 55
<211> LENGTH: 1317
<212> TYPE: DNA
<213> ORGANISM: Artificial
<220> FEATURE:
<223> OTHER INFORMATION: FPOX-33

<400> SEQUENCE: 55

```
atggcgcccc gagccaacac caaaatcatc gtcgtcggcg gcggcggcac aatgggctcg      60
tcgacagccc tacacctcct gcgcgccggc tacacgccga ccaacatcac agtgctcgac     120
acgtacccta tcccttccgc acagtctgca ggctacgacc tgaacaagat cttcggcatc     180
tcaggcgcga acaagcatga cttacaactc tcgcttgagg cgttcgacat gtggaaaaat     240
gatcctctat tcaagccgtt tttccacaat gttggacaga tggaagtctc ttcaacagaa     300
gaaggcatca aacgccttcg ccgcagatac cagtctcttc ccgcgcagg cattgggctc      360
gagaagacga atttcctgct ggaaagtgaa gacgagatcc tggctaaagc gccgcatttc     420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600
```

```
atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317

<210> SEQ ID NO 56
<211> LENGTH: 1317
<212> TYPE: DNA
<213> ORGANISM: Artificial
<220> FEATURE:
<223> OTHER INFORMATION: FPOX-34

<400> SEQUENCE: 56
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggccatgacc tgaacaagat cttcggcatc    180
tcaggcgcga acaagcatga cttacaactc tcgcttgagg cgttcgacat gtggaaaaat    240
gatcctctat tcaagccgtt tttccacaat gttggacaga tggaagtctc ttcaacagaa    300
gaaggcatca aacgccttcg ccgcagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga aagacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317
```

<210> SEQ ID NO 57
<211> LENGTH: 1317
<212> TYPE: DNA
<213> ORGANISM: Artificial
<220> FEATURE:
<223> OTHER INFORMATION: FPOX-35

<400> SEQUENCE: 57

| | | | | | |
|---|---|---|---|---|---|
| atggcgcccc | gagccaacac | caaaatcatc | gtcgtcggcg | gcggcggcac | aatgggctcg | 60 |
| tcgacagccc | tacacctcct | gcgcgccggc | tacacgccgt | ccaacatcac | agtgctcgac | 120 |
| acgtacccta | tcccttccgc | acagtctgca | ggctacgacc | tgaacaaggt | cttcggcatc | 180 |
| tcaggcgcga | acaagcatga | cttacaactc | tcgcttgagg | cgttcgacat | gtggaaaaat | 240 |
| gatcctctat | tcaagccgtt | tttccacaat | gttggacaga | tggaagtctc | ttcaacagaa | 300 |
| gaaggcatca | aacgccttcg | ccgcagatac | cagtctcttc | tccgcgcagg | cattgggctc | 360 |
| gagaagacga | atttcctgct | ggaaagtgaa | gacgagatcc | tggctaaagc | gccgcatttc | 420 |
| acgcgggagc | agattaaagg | ctggaaaggg | ctgttctgtg | gcgacggcgg | ttggctcgct | 480 |
| gcagccaaag | ccatcaatgc | catcgggcag | ttcctcaagg | aacagggcgt | caagtttgga | 540 |
| tttggcgagg | ccggcacgtt | caaaaagcca | ctcttcgccg | atgccgacga | aagacgtgc  | 600 |
| atcggcgtcg | aaactgtaga | cggcacaaaa | tactacgccg | acaaggtcgt | tctagcagct | 660 |
| ggtgcctgga | gttcgacgtt | ggtcgatctg | aggagcagt  | gcgttcaaa  | ggcctgggtc | 720 |
| tttgcccaca | tccaactgac | gcccgctgaa | gcagccgcgt | acaagaacac | tcctgttata | 780 |
| tacgacggtg | actatgggtt | tttcattgag | ccggacgaga | acggcatcat | aaaagtctgc | 840 |
| gacgaattcc | ctggcttcac | gcacttcaag | atgcaccagc | cgtacggctc | accggtgccc | 900 |
| aaattgatct | ctgtgcctcg | ctcccatgcg | aagcacccca | cagatacata | cccgcacgcg | 960 |
| tcggaggtca | ccatcaaaaa | ggctatcaac | cggttcctgc | cgaggttcaa | tgacaaggaa | 1020 |
| ctgtttaaca | gggccatgtg | ctggtgcacc | gataccgcgg | atgcaaatct | gcttgtttgt | 1080 |
| gagcatccac | gctggaaggg | gttttatctt | gcaacagggg | acagcgggca | ttcgttcaag | 1140 |
| ttgctgccga | atattggaaa | gcacgttgtc | gagttattgg | aggggaggct | ggaaagtgtg | 1200 |
| tttaaggatg | cttggaggtg | gaggcctggc | agtggggatg | cattaaagag | tagacgggct | 1260 |
| gcgcctgcga | aggacctggc | ggatatgccg | gggtggagga | atgaggcaaa | gatgtag    | 1317 |

<210> SEQ ID NO 58
<211> LENGTH: 1317
<212> TYPE: DNA
<213> ORGANISM: Artificial
<220> FEATURE:
<223> OTHER INFORMATION: FPOX-36

<400> SEQUENCE: 58

| | | | | | |
|---|---|---|---|---|---|
| atggcgcccc | gagccaacac | caaaatcatc | gtcgtcggcg | gcggcggcac | aatgggctcg | 60 |
| tcgacagccc | tacacctcct | gcgcgccggc | tacacgccgt | ccaacatcac | agtgctcgac | 120 |
| acgtacccta | tcccttccgc | acagtctgca | ggctacgacc | tgaacaagat | cttcggcatc | 180 |
| tcaggcgcga | acaagcatga | cttacaactc | tcgcttgagg | cgttcgacat | gtggaaaaat | 240 |
| gatcctctat | tcaagccgtt | tttccacaat | gttggacaga | tggacgtctc | ttcaacagaa | 300 |
| gaaggcatca | aaaagcttcg | ccgcagatac | cagtctcttc | tccgcgcagg | cattgggctc | 360 |
| gagaagacga | atttcctgct | ggaaagtgaa | gacgagatcc | tggctaaagc | gccgcatttc | 420 |
| acgcgggagc | agattaaagg | ctggaaaggg | ctgttctgtg | gcgacggcgg | ttggctcgct | 480 |

```
gcagccaaag ccatcaatgc catcgggcag ttcctcaagg aacagggcgt caagtttgga      540
tttggcgagg ccggcacgtt caaaaagcca ctcttcgccg atgccgacga aagacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga tgaggcaaa gatgtag         1317
```

<210> SEQ ID NO 59
<211> LENGTH: 1317
<212> TYPE: DNA
<213> ORGANISM: Artificial
<220> FEATURE:
<223> OTHER INFORMATION: FPOX-37

<400> SEQUENCE: 59

```
atggcgcccc gagccaacac caaaatcatc gtcgtcggcg gcggcggcac aatgggctcg       60
tcgacagccc tacacctcct gcgcgccggc tacacgccgt ccaacatcac agtgctcgac      120
acgtacccta tcccttccgc acagtctgca ggctacgacc tgaacaagat cttcggcatc      180
tcaggcgcga acaagcatga cttacaactc tcgcttgagg cgttcgacat gtggaaaaat      240
gatcctctat tcaagccgtt tttccacaat gttggacaga tggacgtctc ttcaacagaa      300
gaaggcatca aacgccttcg ccgcagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg cgacggcgg ttggctcgct       480 gcagccaaag ccatcaatgc catcgggcag ttcctcaagg aacagggcgt caagtttgga      540
tttggcgagg ccggcacgtt caaaaagcca ctcttcgccg atgccgacga aagacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
```

-continued

| | |
|---|---|
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 60
<211> LENGTH: 1317
<212> TYPE: DNA
<213> ORGANISM: Artificial
<220> FEATURE:
<223> OTHER INFORMATION: FPOX-38

<400> SEQUENCE: 60

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggctacgacc tgaacaagat cttcggcatc | 180 |
| tcaggcgcga acaagcatga cttacaactc tcgcttgagg cgttcgacat gtggaaaaat | 240 |
| gatcctctat tcaagccgtt tttccacaat gttggacaga tggacgtctc ttcaacagaa | 300 |
| gaaggcatca aaaagcttcg caaaagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atagcaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 61
<211> LENGTH: 1317
<212> TYPE: DNA
<213> ORGANISM: Artificial
<220> FEATURE:
<223> OTHER INFORMATION: FPOX-39

<400> SEQUENCE: 61

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggctacgacc tgaacaagat cttcggcatc | 180 |
| tcaggcgcga acaagcatga cttacaactc tcgcttgagg cgttcgacat gtggaaaaat | 240 |
| gatcctctat tcaagccgtt tttccacaat gttggacaga tggaagtctc ttcaacagaa | 300 |
| gaaggcatca aaaagcttcg caaaagatac cagtctcttc tccgcgcagg cattgggctc | 360 |

```
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga aagacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atagcaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag       1317
```

<210> SEQ ID NO 62
<211> LENGTH: 1317
<212> TYPE: DNA
<213> ORGANISM: Artificial
<220> FEATURE:
<223> OTHER INFORMATION: FPOX-40

<400> SEQUENCE: 62

```
atggcgcccc gagccaacac caaaatcatc gtcgtcggcg gcggcggcac aatgggctcg       60
tcgacagccc tacacctcct gcgcgccggc tacacgccgt ccaacatcac agtgctcgac      120
acgtacccta tccctccgc acagtctgca ggctacgacc tgaacaagat cttcggcatc       180
tcaggcgcga acaagcatga cttacaactc tcgcttgagg cgttcgacat gtggaaaaat      240
gatcctctat tcaagccgtt tttccacaat gttggacaga tggacgtctc ttcaacagaa      300
gaaggcatca aacgccttcg caaaagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga aagacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atagcaatct gcttgtttgt     1080
```

| | |
|---|---|
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 63
<211> LENGTH: 1317
<212> TYPE: DNA
<213> ORGANISM: Artificial
<220> FEATURE:
<223> OTHER INFORMATION: FPOX-41

<400> SEQUENCE: 63

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggctacgacc tgaacaagat cttcggcatc | 180 |
| tcaggcgcga acaagcatga cttacaactc tcgcttgagg cgttcgacat gtggaaaaat | 240 |
| gatcctctat tcaagccgtt tttccacaat gttggacaga tggacgtctc ttcaacagaa | 300 |
| gaaggcatca aaaagcttcg ccgcagatac cagtctcttc tccgcgcagg cattgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcacccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atagcaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 64
<211> LENGTH: 1317
<212> TYPE: DNA
<213> ORGANISM: Artificial
<220> FEATURE:
<223> OTHER INFORMATION: FPOX-42

<400> SEQUENCE: 64

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggctacgacc tgaacaagat cttcggcatc | 180 |
| tcaggcgcga acaagcatga cttacaactc tcgcttgagg cgttcgacat gtggaaaaat | 240 |

```
gatcctctat tcaagccgtt tttccacaat gttggacaga tggacgtctc ttcaacagaa      300
gaaggcatca aacgccttcg ccgcagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga gaagacgtgc      600
atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atagcaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga tgaggcaaa gatgtag        1317
```

<210> SEQ ID NO 65
<211> LENGTH: 1317
<212> TYPE: DNA
<213> ORGANISM: Artificial
<220> FEATURE:
<223> OTHER INFORMATION: FPOX-43

<400> SEQUENCE: 65

```
atggcgcccc gagccaacac caaaatcatc gtcgtcggcg gcggcggcac aatgggctcg       60
tcgacagccc tacacctcct gcgcgccggc tacacgccga ccaacatcac agtgctcgac      120
acgtacccta tccccttccgc acagtctgca ggctacgacc tgaacaagat cttcggcatc      180
tcaggcgcga acaagcatga cttacaactc tcgcttgagg cgttcgacat gtggaaaaat      240
gatcctctat tcaagccgtt tttccacaat gttggacaga tggacgtctc ttcaacagaa      300
gaaggcatca aacgccttcg ccgcagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga gaagacgtgc      600
atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
```

| | |
|---|---|
| tcggaggtca ccatcaaaaa ggctatcaac cggttcctgc cgaggttcaa tgacaaggaa | 1020 |
| ctgtttaaca gggccatgtg ctggtgcacc gataccgcgg atagcaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 66
<211> LENGTH: 1317
<212> TYPE: DNA
<213> ORGANISM: Artificial
<220> FEATURE:
<223> OTHER INFORMATION: FPOX-44

<400> SEQUENCE: 66

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |
| acgtacccta tcccttccgc acagtctgca ggccatgacc tgaacaagat cttcggcatc | 180 |
| tcaggcgcga acaagcatga cttacaactc tcgcttgagg cgttcgacat gtggaaaaat | 240 |
| gatcctctat tcaagccgtt ttttccacaat gttggacaga tggacgtctc ttcaacagaa | 300 |
| gaaggcatca aacgccttcg ccgcagatac cagtctcttc ccgcgcaggc attgggctc | 360 |
| gagaagacga atttcctgct ggaaagtgaa gacgagatcc tggctaaagc gccgcatttc | 420 |
| acgcgggagc agattaaagg ctggaaaggg ctgttctgtg gcgacggcgg ttggctcgct | 480 |
| gcagccaaag ccatcaatgc catcgggcag ttcctcaagg aacagggcgt caagtttgga | 540 |
| tttggcgagg ccggcacgtt caaaaagcca ctcttcgccg atgccgacga aagacgtgc | 600 |
| atcggcgtcg aaactgtaga cggcacaaaa tactacgccg acaaggtcgt tctagcagct | 660 |
| ggtgcctgga gttcgacgtt ggtcgatctg gaggagcagt gcgtttcaaa ggcctgggtc | 720 |
| tttgcccaca tccaactgac gcccgctgaa gcagccgcgt acaagaacac tcctgttata | 780 |
| tacgacggtg actatgggtt tttcattgag ccggacgaga acggcatcat aaaagtctgc | 840 |
| gacgaattcc ctggcttcac gcacttcaag atgcaccagc cgtacggctc accggtgccc | 900 |
| aaattgatct ctgtgcctcg ctcccatgcg aagcaccccca cagatacata cccgcacgcg | 960 |
| tcggaggtca ccatcaaaaa ggctatcaac cggttcctgc cgaggttcaa tgacaaggaa | 1020 |
| ctgtttaaca gggccatgtg ctggtgcacc gataccgcgg atagcaatct gcttgtttgt | 1080 |
| gagcatccac gctggaaggg gttttatctt gcaacagggg acagcgggca ttcgttcaag | 1140 |
| ttgctgccga atattggaaa gcacgttgtc gagttattgg aggggaggct ggaaagtgtg | 1200 |
| tttaaggatg cttggaggtg gaggcctggc agtggggatg cattaaagag tagacgggct | 1260 |
| gcgcctgcga aggacctggc ggatatgccg gggtggagga atgaggcaaa gatgtag | 1317 |

<210> SEQ ID NO 67
<211> LENGTH: 1317
<212> TYPE: DNA
<213> ORGANISM: Artificial
<220> FEATURE:
<223> OTHER INFORMATION: FPOX-45

<400> SEQUENCE: 67

| | |
|---|---|
| atggcgcccc gagccaacac caaaatcatc gtcgtcggcg gcggcggcac aatgggctcg | 60 |
| tcgacagccc tacacctcct gcgcgccggc tacacgccgt ccaacatcac agtgctcgac | 120 |

```
acgtacccta tcccttccgc acagtctgca ggctacgacc tgaacaaggt cttcggcatc      180
tcaggcgcga acaagcatga cttacaactc tcgcttgagg cgttcgacat gtggaaaaat      240
gatcctctat tcaagccgtt tttccacaat gttggacaga tggacgtctc ttcaacagaa      300
gaaggcatca aacgccttcg ccgcagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga aagacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atagcaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag        1317
```

<210> SEQ ID NO 68
<211> LENGTH: 1317
<212> TYPE: DNA
<213> ORGANISM: Artificial
<220> FEATURE:
<223> OTHER INFORMATION: FPOX-46

<400> SEQUENCE: 68

```
atggcgcccc gagccaacac caaaatcatc gtcgtcggcg gcggcggcac aatgggctcg       60
tcgacagccc tacacctcct gcgcgccggc tacacgccgt ccaacatcac agtgctcgac      120
acgtacccta tcccttccgc acagtctgca ggctacgacc tgaacaagat cttcggcatc      180
tcaggcgcga acaagcatga cttacaactc tcgcttgagg cgttcgacat gtggaaaaat      240
gatcctctat tcaagccgtt tttccacaat gttggacaga tggaagtctc ttcaacagaa      300
gaaggcatca aacgccttcg ccgcagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga aagacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
```

```
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atagcaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag        1317
```

<210> SEQ ID NO 69
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 69
caattaatca tccggctcgt a                                                  21

<210> SEQ ID NO 70
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 70
cttctgagtt cggcatgggg                                                    20

<210> SEQ ID NO 71
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 71
tcaagtttgg atttggcga                                                     19

<210> SEQ ID NO 72
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 72
cctgaacaaa atcttcggca tctcactgcg c                                       31

<210> SEQ ID NO 73
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 73
gtaagtcagg cttgttgcgc atgatgatgc c                                       31

<210> SEQ ID NO 74
<211> LENGTH: 30

```
<212> TYPE: DNA
<213> ORGANISM: Artificial
<220> FEATURE:
<223> OTHER INFORMATION: An artificially synthesized primer sequence

<400> SEQUENCE: 74
aaaatcttcg gcatctcact ggcgaacaag                                    30

<210> SEQ ID NO 75
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 75
gagttgtaag tcaggcttgt tcgccagtga                                    30

<210> SEQ ID NO 76
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 76
aacaaaatct tcggcatctc aggcgcgaac                                    30

<210> SEQ ID NO 77
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 77
ttgtaagtca ggcttgttcg cgcctgagat                                    30

<210> SEQ ID NO 78
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 78
gaacaagcct gacttacaac tctgccttga g                                  31

<210> SEQ ID NO 79
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 79
ccacatgtcc agcgcctcaa ggcagagttg                                    30

<210> SEQ ID NO 80
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 80
```

```
gaacaagcct gacttacaac tcagccttga g                                    31

<210> SEQ ID NO 81
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 81
ccacatgtcc agcgcctcaa ggctgagttg                                      30

<210> SEQ ID NO 82
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 82
catgagatac cagtctcttc tcaacgcagg c                                    31

<210> SEQ ID NO 83
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 83
gtcttctcga gcccaatgcc tgcgttgaga ag                                   32

<210> SEQ ID NO 84
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 84
catgagatac cagtctcttc tccgcgcagg c                                    31

<210> SEQ ID NO 85
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 85
gtcttctcga gcccaatgcc tgcgcggaga ag                                   32

<210> SEQ ID NO 86
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 86
gaaggcatca aaaagcttcg caaaagatac                                      30

<210> SEQ ID NO 87
<211> LENGTH: 30
<212> TYPE: DNA
<213> ORGANISM: Artificial
```

```
<220> FEATURE:
<223> OTHER INFORMATION: An artificially synthesized primer sequence

<400> SEQUENCE: 87
gcggagaaga gactggtatc ttttgcgaag                                30

<210> SEQ ID NO 88
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 88
gaggcggccg acatgtggaa aaatgatcct cta                            33

<210> SEQ ID NO 89
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 89
catgtcggcc gcctcaaggc tgagttgtaa g                              31

<210> SEQ ID NO 90
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 90
cttacaactc tcgcttgagg cgttcgacat g                              31

<210> SEQ ID NO 91
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 91
gaggatcatt tttccacatg tcgaacgcct c                              31

<210> SEQ ID NO 92
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 92
ctgcgcgccg gctacacgcc gaccaacatc                                30

<210> SEQ ID NO 93
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 93
cgtgtcgagc actgtgatgt tggtcggcgt                                30
```

```
<210> SEQ ID NO 94
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 94
ccttccgcac agtctgcagg ccatgacctg                                     30

<210> SEQ ID NO 95
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 95
gccgaagatc ttgttcaggt catggcctgc                                     30

<210> SEQ ID NO 96
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 96
gcaggctacg acctgaacaa ggtcttcggc                                     30

<210> SEQ ID NO 97
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 97
gttcgcgcct gagatgccga agaccttgtt                                     30

<210> SEQ ID NO 98
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 98
ggcatctcag gcgcgaacaa gcatgactta                                     30

<210> SEQ ID NO 99
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 99
ctcaaggctg agttgtaagt catgcttgtt                                     30

<210> SEQ ID NO 100
<211> LENGTH: 30
<212> TYPE: DNA
<213> ORGANISM: Artificial
<220> FEATURE:
<223> OTHER INFORMATION: An artificially synthesized primer sequence
```

<400> SEQUENCE: 100
ttccacaatg ttggacagat ggaagtctct                                30

<210> SEQ ID NO 101
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 101
gccttcttct gttgaagaga cttccatctg                                30

<210> SEQ ID NO 102
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 102
tcaacagaag aaggcatcaa acgccttcgc                                30

<210> SEQ ID NO 103
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 103
gagactggta tcttttgcga aggcgtttga t                              31

<210> SEQ ID NO 104
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 104
gagactggta tctgcggcga aggcgtttga t                              31

<210> SEQ ID NO 105
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 105
gaaggcatca aaaagcttcg ccgcagatac                                30

<210> SEQ ID NO 106
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 106
gcggagaaga gactggtatc tgcggcgaag                                30

<210> SEQ ID NO 107

```
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 107
tggtgcaccg ataccgcgga tagcaatctg                                        30

<210> SEQ ID NO 108
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 108
gatgctcaca aacaagcaga ttgctatccg c                                      31
```

METHOD FOR MEASURING GLYCATED HEMOGLOBIN

TECHNICAL FIELD

The present invention relates to methods for measuring glycated hemoglobin in samples.

BACKGROUND ART

Glycated proteins are contained in biological samples such as body fluid and hair, and body fluid includes blood in a living body, and such. The concentration of glycated proteins present in the blood depends on the concentration of sugars such as glucose dissolved in the serum, and recently, in the field of clinical diagnosis, measurement of the concentration of hemoglobin A1c (hereinafter, HbA1c; Non-Patent Document 1), which is a glycated protein in the blood, is being used to diagnose and monitor diabetes mellitus. As a method for measuring this HbA1c, instrumental analytical methods using high-performance liquid chromatography (HPLC) (Non-Patent Document 2), immunoassays using antigen-antibody reactions (for example, Non-Patent Document 3), and such had been known, but in recent years, enzymatic assays have been developed, and for example, a method using a protease and a glycated peptide oxidase (Patent Document 1) has been developed. Enzymatic assays can be applied to versatile automated analyzers, and since the operations are also simple, they are being developed actively.

The glycated peptide oxidase used in enzymatic assays is an enzyme that catalyzes the reaction which produces a sugar osone (an α-keto aldehyde), a peptide, and hydrogen peroxide by oxidatively cleaving, in the presence of oxygen molecules, the C—N bond in the ketose derivative produced by Amadori rearrangement of glucosylamine produced by the reaction between the hemiacetal of glucose and the N-terminal amino group of a peptide.

In the case of enzymatic assays, a method is known in which HbA1c is first degraded with a protease, and α-glycated valyl histidine (hereinafter, denoted as α-FVH) is produced from the N terminus of the β-chain of hemoglobin; next, glycated peptide oxidase is made to act on the produced α-FVH to produce hydrogen peroxide, a quinone dye is produced in the presence of peroxidase by the produced hydrogen peroxide, and the produced amount is determined by colorimetry using a spectrophotometer (Patent Document 1).

However, the glycated peptides to which conventionally-known glycated peptide oxidases (for example, Patent Documents 2, 3, 4, and 5, and Non-Patent Document 4) can act are ordinarily dipeptides, the largest being hexapeptides (Patent Documents 6 and 7), and glycated peptide oxidases that act on glycated peptides with longer amino acid chain length and on glycated proteins have not been known. Therefore, as described above, with regard to enzyme assays, the only method that has been reported is the method which comprises making a protease act on a glycated protein, making a glycated peptide oxidase act on the produced glycated peptide, and measuring the generated hydrogen peroxide.

With regard to this method which comprises making a protease act on glycated hemoglobin, making a glycated peptide oxidase act on the produced glycated peptide, and measuring the generated hydrogen peroxide, in case other measurements besides the glycated hemoglobin measurements are taken simultaneously using an automatic analyzer or such, the protease in the reagent for measuring glycated hemoglobin may act on other reagents and may affect the measured values.

PRIOR ART DOCUMENTS

Patent Documents

[Patent Document 1] Japanese Patent Application Kokai Publication No. (JP-A) 2001-95598 (unexamined, published Japanese patent application).
[Patent Document 2] International Publication No. WO 2004/104203 pamphlet.
[Patent Document 3] JP-A (Kokai) 2003-235585.
[Patent Document 4] International Publication No. WO 2004/038033 pamphlet.
[Patent Document 5] International Publication No. WO 2010/041715 pamphlet.
[Patent Document 6] International Publication No. WO 2004/038034 pamphlet.
[Patent Document 7] International Publication No. WO 2008/108385 pamphlet.

Non-Patent Documents

[Non-Patent Document 1] Clin Chem Lab Med, Vol. 36, p. 299-308 (1998).
[Non-Patent Document 2] Diabetes, Vol. 27(2), p. 102-107 (1978).
[Non-Patent Document 3] Nihon Rinsho Kensa Jidoka Gakkai Kaishi (Journal of the Japan Society for Clinical Laboratory Automation), Vol. 18, No. 4, p. 620 (1993).
[Non-Patent Document 4] Appl Microbiol Biotechnol, Vol. 78, No. 5, p. 775-781 (2008).

SUMMARY OF THE INVENTION

Problems to be Solved by the Invention

An objective of the present invention is to provide a method for measuring glycated hemoglobin, which comprises directly oxidizing glycated hemoglobin and measuring a substance produced or consumed by the oxidation, without making a protease act on glycated hemoglobin.

Means for Solving the Problems

The present invention relates to the following (1) to (4).
(1) A method for measuring glycated hemoglobin in a sample, wherein the method comprises directly oxidizing glycated hemoglobin in a sample, and measuring a substance produced or consumed by the oxidation.
(2) The method of (1), wherein the glycated hemoglobin is directly oxidized using an enzyme.
(3) The method of (1) or (2), wherein the produced substance is hydrogen peroxide.
(4) The method of (1) to (3), wherein the glycated hemoglobin is hemoglobin A1c.

Effects of the Invention

The present invention provides methods for measuring glycated hemoglobin, which comprises directly oxidizing glycated hemoglobin in a sample, and measuring a substance produced or consumed by the oxidation.

MODE FOR CARRYING OUT THE INVENTION

Figure 1:
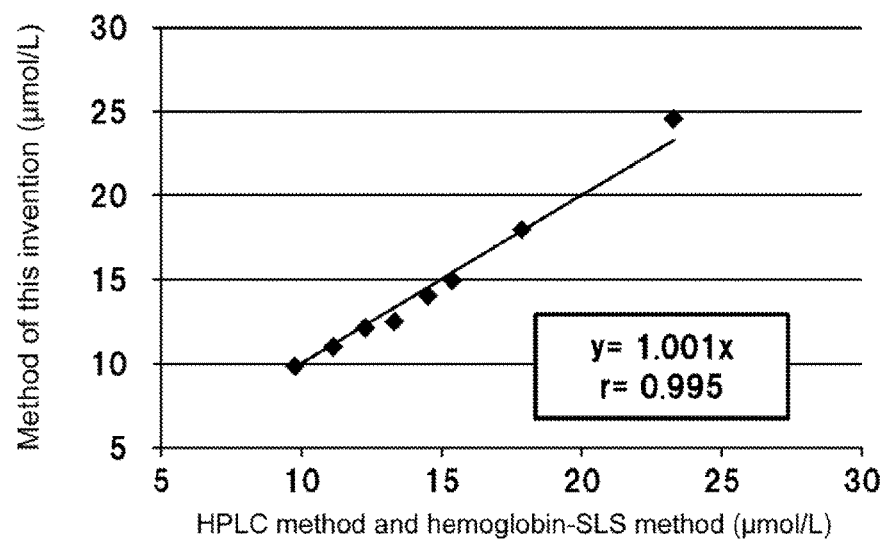
FIG. 1 shows a graph indicating the correlation between HbA1c concentrations determined by the HbA1c measurement method of the present invention which directly oxidizes HbA1c using FPOX-19, and HbA1c concentrations determined by the HbA1c measurement method that uses both of the HPLC method (KO500 method) and the hemoglobin-SLS method.

1. Method of the Present Invention for Measuring Glycated Hemoglobin

A measurement method of the present invention is a method for measuring glycated hemoglobin, which comprises directly oxidizing glycated hemoglobin and measuring a substance produced or consumed by the oxidation. HbA1c is preferred as a glycated hemoglobin in the present invention. While the method for directly oxidizing glycated hemoglobin may be any method as long as glycated hemoglobin can be oxidized directly, a method for oxidation that uses an enzyme is preferred.

The measurement method of the present invention is described below.

(Samples and Objects to be Measured)

The sample used in the measurement method of the present invention is not particularly limited so long as it contains glycated hemoglobin, and examples include biological samples such as whole blood, plasma, serum, blood cells, cell samples, urine, spinal fluid, sweat, tear fluid, saliva, skin, mucous membrane, and hair. As a sample, whole blood, plasma, serum, blood cells and such are preferred, and whole blood, blood cells, and such are particularly preferred. Whole blood includes samples of whole blood-derived blood cell fractions admixed with plasma. With regard to these samples, samples subjected to pretreatments such as hemolysis, separation, dilution, concentration, and purification can be used.

Hemoglobin is a hemeprotein consisting of two of each of the two types of subunits, the α-chain and the β-chain, and has a molecular weight of 64,000. The sequence of the three amino acids at the N terminus of the α-chain of hemoglobin is valine-leucine-serine and the sequence of the three amino acids at the N terminus of the β-chain is valine-histidine-leucine. HbA1c is defined as hemoglobin in which the N-terminal valine residue of the β-chain is particularly glycated; however, hemoglobin is known to have multiple glycation sites within the molecule, including the N terminus of the α-chain (The Journal of Biological Chemistry (1980), 256, 3120-3127).

(Measurement Method)

In the present invention, glycated hemoglobin to be measured in a sample can be measured, for example, by sequentially performing the following steps (i) and (ii):
(i) oxidizing glycated hemoglobin by making an enzyme act on glycated hemoglobin in the sample; and
(ii) measuring a substance produced or consumed in the above-mentioned step (i).

While the enzyme used in step (i) may be any enzyme as long as glycated hemoglobin can be oxidized directly, for example, the following enzymes may be used. Examples include
[1] proteins having the amino acid sequence represented by any one of SEQ ID NOs: 3 to 34 (they are called FPOX-18A, FPOX-18B, FPOX-18C, FPOX-18D, FPOX-19, FPOX-20, FPOX-21, FPOX-22, FPOX-23, FPOX-24, FPOX-25, FPOX-26, FPOX-27, FPOX-28, FPOX-29, FPOX-30, FPOX-31, FPOX-32, FPOX-33, FPOX-34, FPOX-35, FPOX-36, FPOX-37, FPOX-38, FPOX-39, FPOX-40, FPOX-41, FPOX-42, FPOX-43, FPOX-44, FPOX-45, and FPOX-46, respectively); and
[2] proteins comprising an amino acid sequence having 90% or higher homology to the amino acid sequence represented by any one of SEQ ID NOs: 3 to 34, and also having the activity of directly oxidizing glycated hemoglobin (hereinafter referred to as the glycated hemoglobin oxidase activity). Hereinafter, proteins having glycated hemoglobin oxidase activity are referred to as glycated hemoglobin oxidases. One type of the glycated hemoglobin oxidases can be used individually or two or more types can be used in combination.

In order for the proteins used in the method of the present invention to have glycated hemoglobin oxidase activity, desirably, the proteins have 90% or higher, preferably 94% or higher, more preferably 96% or higher, even more preferably 98% or higher, particularly preferably 99% or higher homology to the amino acid sequence represented by any one of SEQ ID NOs: 3 to 34.

Homology of amino acid sequences and nucleotide sequences can be determined using the BLAST algorithm by Karlin and Altshul [Pro. Natl. Acad. Sci. USA, 90, 5873 (1993)] or FASTA [Methods Enzymol., 183, 63 (1990)]. Programs called BLASTN and BLASTX have been developed based on this BLAST algorithm [J. Mol. Biol., 215, 403 (1990)]. In case nucleotide sequences are analyzed by BLASTN based on BLAST, parameters are set, for example, at score=100 and wordlength=12. In case amino acid sequences are analyzed by BLASTX based on BLAST, parameters are set, for example, at score=50 and wordlength=3. In case using the BLAST and Gapped BLAST programs, the default parameters of each program are used.

The above-mentioned steps (i) and (ii) can be carried out in an aqueous medium. An aqueous medium is not particularly limited as long as it enables the measuring method of the present invention and examples of the aqueous medium include a deionized water, a distilled water, and a buffer solution; and, a buffer solution is preferred. Examples of a buffer agent to be used in the buffer solution include tris(hydroxymethyl)aminomethane buffer (Tris buffer), a phosphate buffer, a borate buffer, and a Good's buffer.

Examples of the Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxy-3-propanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]-glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

The concentration of the buffer is not particularly limited as long as it is suitable for measurement, and the concentration is preferably 0.001 mol/L to 2.0 mol/L, and more preferably 0.005 mol/L to 1.0 mol/L.

In step (i) mentioned above, a denaturing agent of glycated hemoglobin or an oxidizing agent may coexist. Alternatively, a sample containing glycated hemoglobin can be treated with the denaturing agent or the oxidizing agent in advance. The denaturing agent is not particularly limited, as long as it enables the measurement method of the present invention and examples thereof include a nonionic surfactant, a cationic surfactant, an anionic surfactant, and an amphoteric surfactant. The oxidizing agent is not particularly limited as long as it enables the measurement method of the present invention and examples thereof include potassium iodate, potassium periodate, and potassium bromate.

For the reactions in each step, the reaction temperature is for example, 10° C. to 50° C. and preferably 20° C. to 40° C., and the reaction time is 1 second to 120 minutes, preferably 1 to 90 minutes, and particularly preferably 1 to 60 minutes.

In step (i), products formed in the reaction solution due to the reaction between the glycated hemoglobin and the enzyme include hydrogen peroxide, sugar osone (α-keto aldehyde), and hemoglobin. Furthermore, in step (i), a substance consumed by the reaction between the glycated hemoglobin and the enzyme is, for example, an oxygen molecule. Oxygen molecule consumed in step (i) is measured, for example, by an electrochemical measurement method using an oxygen electrode.

In the method for measuring glycated hemoglobin of the present invention, the method for measuring glycated hemoglobin in a sample, which comprises making glycated hemoglobin oxidase act on glycated hemoglobin in the sample to directly oxidize the glycated hemoglobin, and measuring the thus produced hydrogen peroxide, is preferred. Hydrogen peroxide produced in step (i) of the present invention can be measured using, for example, an optical technique or an electrochemical technique. Examples of the optical technique include an absorbance method and a luminescence method. Specific examples include an optical determination using a reagent for measuring hydrogen peroxide and an electrochemical determination using a hydrogen peroxide electrode.

A reagent for measuring hydrogen peroxide is a reagent for converting the produced hydrogen peroxide into a detectable substance. Examples of the detectable substance include dye and light; and, a dye is preferred.

In case the detectable substance is a dye, the reagent for measuring hydrogen peroxide comprises a peroxidative active substance such as peroxidase and an oxidative coloring chromogen. Examples of the oxidative coloring chromogen include an oxidative coupling-type chromogen and a leuco-type chromogen which are described later.

In case the detectable substance is a light, the reagent for measuring hydrogen peroxide comprises a chemiluminescent substance. A bioluminescent substance is included in a chemiluminescent substance, and examples of the chemiluminescent substance include luminol, isoluminol, lucigenin, an acridinium ester, and an oxalate ester.

In case using a reagent comprising a peroxidative active substance such as peroxidase and an oxidative coloring chromogen as a reagent for measuring hydrogen peroxide, hydrogen peroxide can be measured by reacting hydrogen peroxide with the oxidative coloring chromogen in the presence of a peroxidative active substance to form a dye and then measuring the formed dye. Furthermore, in case using a reagent for measuring hydrogen peroxide which comprises a chemiluminescent substance, hydrogen peroxide can be measured by reacting hydrogen peroxide with a chemiluminescent substance to form photons and then measuring the formed photons.

An oxidative coupling-type chromogen is a chromogen which reacts with hydrogen peroxide in the presence of a peroxidative active substance such as peroxidase to produce a dye by an oxidative coupling reaction. Specific examples of the oxidative coupling-type chromogen include a coupler such as 4-aminoantipyrine, and a phenolic or anilinic hydrogen donor. A coupler and a phenolic or anilinic hydrogen donor compound undergo oxidative coupling in the presence of hydrogen peroxide and a peroxidative active substance to produce a dye.

Examples of a coupler include 4-aminoantipyrine (4-AA) and 3-methyl-2-benzothiazolinone hydrazone.

Examples of a phenolic hydrogen donor include phenol, 4-chlorophenol, 3-methylphenol, and 3-hydroxy-2,4,6-triiodobenzoic acid (HTIB).

Examples of an anilinic hydrogen donor include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, N-ethyl-N-(2-hydroxy-3-sulfopropyl)-4-fluoro-3,5-dimethoxyaniline (F-DAOS), N-[2-(succinylamino)ethyl]-2-methoxy-5-methylaniline (MASE), and N-ethyl-N-[2-(succinylamino)ethyl]-2-methoxy-5-methylaniline (Et-MASE).

A leuco chromogen is a chromogen which produces a dye by itself by reacting with hydrogen peroxide in the presence of a peroxidative active substance such as peroxidase. Specific examples thereof include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4, 4'-bis(dimethylamino)diphenylamine sodium salt (DA-64), 10-(carboxymethylaminocarbonyl)-3,7-bis(dimethylamino) phenothiazine sodium salt (DA-67), 4,4'-bis(dimethylamino)diphenylamine, bis[3-bis(4-chlorophenyl)methyl-4-dimethylaminophenyl]amine (BCMA), N,N,N',N',N'',N''-hexa-3-sulfopropyl-4,4',4''-triaminotriphenylmethane (TPM-PS), diaminobentidine, hydroxyphenylpropionic acid, tetramethylbentidine, and o-phenylenediamine.

In the measurement of hydrogen peroxide, the concentration of the peroxidative active substance is not particularly limited as long as it is suitable for the measurement; and, in case peroxidase is used as a peroxidative active substance, the concentration is preferably 1 U/mL to 100 U/mL and more preferably 2 U/mL to 50 U/mL. The concentration of the oxidative coloring chromogen is not particularly limited as long as it is suitable for measurement; and, it is preferably 0.01 g/L to 10 g/L and more preferably 0.02 g/L to 5 g/L.

In case hydrogen peroxide is measured using a hydrogen peroxide electrode, the electrode to be used is not particularly limited as long as it is a material that allows transfer of electrons with the hydrogen peroxide, and examples thereof include platinum, gold, and silver. As a method for measurement, known methods such as amperometry, potentiometry, and coulometry can be used. By interposing an electron-transfer substance in the reaction between the electrode and the oxidase or substrate, the resulting oxidation or reduction current or its electrical quantity can also be measured.

Any substance having a function of transferring electrons can be used as an electron-transfer substance, and examples thereof include a substance such as a ferrocene derivative and a quinone derivative. Furthermore, the oxidation or reduction current or its electrical quantity obtained by interposing an electron-transfer substance between the electrode and the hydrogen peroxide produced by the oxidase reaction can be measured.

In step (i), a sugar osone (an α-keto aldehyde) is produced together with hydrogen peroxide; therefore, HbA1c in a sample can also be measured by measuring the produced sugar osone (an α-keto aldehyde). By making glucose oxidase act on the α-keto aldehyde and by measuring the produced hydrogen peroxide as well, highly sensitive measurements can be carried out (JP-A (Kokai) 2000-333696).
Method for Producing Glycated Hemoglobin Oxidase An example of a method for producing glycated hemoglobin oxidase which is a protein used in a method of the present invention is shown below.
(Plasmid Extraction)

Expression plasmid pTrc-FPOX-9 of glycated peptide oxidase FPOX-9 represented by the amino acid sequence of SEQ ID NO: 2 is extracted from glycated peptide oxidase FPOX-9-expressing *Escherichia coli* XL1-Blue MRF' strain deposited under Accession No. FERM BP-11026, by using a commercially available plasmid extraction kit.
(Production of Glycated Peptide Oxidase FPOX-15 Expression Plasmid)

Expression plasmid pTrc-FPOX-15 of glycated peptide oxidase FPOX-15 having the amino acid sequence represented by SEQ ID NO: 1 is constructed through site-specific introduction of amino acid substitutions by a PCR method using the pTrcFPOX-9 expression plasmid as a template DNA and a primer pair in which a codon corresponding to the target amino acid position is replaced with a codon corresponding to the substituting amino acid.

(Construction of Glycated Hemoglobin Oxidases by Site-Specific Amino Acid Substitutions)

Site-specific amino acid substitutions are introduced to pTrc-FPOX-15 by a method similar to that described above to construct expression plasmids for each of the glycated hemoglobin oxidases, which are FPOX-18A having the amino acid sequence represented by SEQ ID NO: 3, FPOX-18B having the amino acid sequence represented by SEQ ID NO: 4, FPOX-18C having the amino acid sequence represented by SEQ ID NO: 5, FPOX-18D having the amino acid sequence represented by SEQ ID NO: 6, FPOX-19 having the amino acid sequence represented by SEQ ID NO: 7, and FPOX-20 having the amino acid sequence represented by SEQ ID NO: 8.

By introducing site-specific amino acid substitutions to the FPOX-19 expression plasmid pTrc-FPOX-19 by a method similar to that described above, expression plasmids for each of the glycated hemoglobin oxidases FPOX-21 to 46 having the amino acid sequence represented by SEQ ID NOs: 9 to 34, respectively, are constructed.

The constructed glycated hemoglobin oxidase expression plasmids are used to transform *E. coli* strains to produce recombinant glycated hemoglobin oxidase-expressing *E. coli* strains. The recombinant glycated hemoglobin oxidase-expressing *E. coli* strains are inoculated into Luria-Bertani (hereinafter written as LB) medium containing 50 to 100 mg/L ampicillin, and are shake-cultured at 37° C. After growing the culture to $OD_{600}$=0.4 to 0.8, isopropyl-β-thiogalactoside (hereinafter written as IPTG) is added to make a final concentration of 0.1 to 1 mmol/L, and shake-culturing is continued at 37° C. for 5 to 24 hours. After culturing, the bacterial cells are collected by centrifugation at 8000 rpm for 10 to 30 minutes.

The bacterial cells obtained as described above are suspended in a buffer, and disrupted by sonication for one to ten minutes, and after centrifugation, the supernatants are fractionated to prepare crude extract solutions of the enzymes. Purified enzymes are prepared from the crude extract solutions by techniques such as anion exchange column chromatography and ammonium sulfate precipitation, using as indicators the enzyme activity and the color tone presented by the coenzyme flavin-adenine dinucleotide (hereinafter written as FAD) harbored by the enzymes.

Concentrations of the purified enzymes are determined by measuring the absorbance at 452 nm which is derived from FAD, a coenzyme of the protein, comparing the obtained absorbance to the results in the calibration curve that indicates the relationship between glycated hemoglobin oxidase concentration and absorbance, which was prepared in advance using glycated peptide oxidase with known activity.
(Method for Determining Glycated Hemoglobin Oxidase Activity)

In the measurement method of the present invention, glycated hemoglobin oxidase activity can be measured, for example, by the following method.
(Reagent for Activity Measurement)
Solution A: 0.1 mol/L MOPS buffer (pH6.8)
Solution B: Color developing agent
  24 mmol/L DA-67 solution in dimethylformamide (DMF)
Solution C: Peroxidase solution
  1 kU/L peroxidase solution in 10 mmol/L phosphate buffer (pH7.0)
Solution D: Substrate solution
  10 g/L aqueous hemoglobin solution
Solution E: Denaturant solution
  aqueous solution of 5 g/L potassium iodate and 50% (v/v) surfactant (AMPHITOL 20N)

Solution F: Enzyme solution
0.5 to 1.0 U/mL glycated hemoglobin oxidase solution in 10 mmol/L phosphate buffer (pH7.0)
(Measurement Procedure)

(i) 4 μL of Solution E is mixed into 40 μL of Solution D, and the mixture is incubated at 37° C. for 10 minutes.

(ii) To 10 mL of Solution A, 12.6 μL of Solution B and 35 μL of Solution C are added, the obtained solution is dispensed into each well of a 96-well plate at 190 μL per sample, then 40 μL of a solution produced by mixing Solutions D and E, and 20 μL of Solution F are added and mixed, and the absorbance of the solution immediately after mixing is measured at 660 nm (main wavelength)/750 nm (sub-wavelength) using a fully automated microplate EIA analyzer; this is followed by enzyme reaction while incubating at 37° C. for 60 to 120 minutes, the absorbance of the obtained solution is measured at 660 nm (main wavelength)/ 750 nm (sub-wavelength) and the change in absorbance before and after the enzyme reaction is determined. Furthermore, similar measurements are performed using distilled water instead of Solution D where the change in absorbance before and after the enzyme reaction is set as a blank value, and by subtracting the blank value from the value for the change in absorbance before and after enzyme reaction in the measurement using solution D, the absorbance due to the enzyme reaction can be measured, and this can be used as an indicator for glycated hemoglobin oxidase activity.

The above-mentioned steps (i) and (ii) may be carried out in an aqueous medium. Examples of the aqueous medium include the aforementioned aqueous medium and a buffer is preferred. The buffer concentration may be, for example, the aforementioned buffer concentration.

For the reactions in each step, the reaction temperature is for example, 10° C. to 50° C. and preferably 20° C. to 40° C., and the reaction time is 1 second to 120 minutes, preferably 1 to 90 minutes, and particularly preferably 1 to 60 minutes.

All prior art documents cited herein are incorporated by reference into this description.

EXAMPLES

Herein below, Examples are indicated, but the present invention is not to be construed as being limited thereto. Reagents and enzymes of the following manufacturers were used in the present Examples:
potassium dihydrogenphosphate (Wako Pure Chemical Industries), dibasic potassium phosphate (Wako Pure Chemical Industries), DA-67 (manufactured by Wako Pure Chemical Industries), peroxidase (manufactured by TOYOBO), MOPS (manufactured by Dojindo Laboratories), dimethylformamide (manufactured by Wako Pure Chemical Industries), potassium iodate (manufactured by Wako Pure Chemical Industries), Luria-Bertani miller medium (LB medium) (manufactured by Becton, Dickinson and Company), KOD-Plus-(DNA polymerase; manufactured by TOYOBO), Dpn I (restriction enzyme; manufactured by New England Biolabs), Competent high DH5α (*E. coli* competent cells; manufactured by TOYOBO), Hemoglobin B-Test Wako (kit for measuring hemoglobin concentration; manufactured by Wako Pure Chemical Industries)

[Example 1] Construction of a Protein Having Glycated Hemoglobin Oxidase Activity by Introduction of Site-Specific Amino Acid Substitutions Glycated peptide oxidase FPOX-9-expressing *E. coli* XL1-Blue MRF strain deposited under Accession No. FERM BP-11026 was inoculated into 3 mL of LB medium containing 50 mg/L ampicillin, and shaking culture was performed overnight at 37° C. The culture solution was centrifuged at 8,000 rpm for 2 minutes to collect the bacterial cells. Expression plasmid pTrc-FPOX-9 comprising a DNA consisting of the nucleotide sequence represented by SEQ ID NO: 36, which expresses glycated peptide oxidase FPOX-9 having the amino acid sequence represented by SEQ ID NO: 2 was extracted from the obtained bacterial cells using "Wizard Plus SV Minipreps DNA Purification" manufactured by Promega.

Using the method described in International Publication No. WO 2010/041715 pamphlet, pTrc-FPOX-15 comprising a DNA consisting of the nucleotide sequence represented by SEQ ID NO: 35 was produced from pTrc-FPOX-9 and by transforming the *E. coli* DH5α strain using pTrc-FPOX-15, an *E. coli* strain that expresses glycated peptide oxidase FPOX-15 having the amino acid sequence represented by SEQ ID NO: 1 was produced. The bacterial strain was inoculated into 3 mL of LB medium containing 50 mg/L ampicillin, and shaking culture was performed overnight at 37° C. The culture solution was centrifuged at 8,000 rpm for 2 minutes to collect the bacterial cells. The FPOX-15 expression plasmid pTrc-FPOX-15 was extracted from the obtained bacterial cells using "Wizard Plus SV Minipreps DNA Purification" manufactured by Promega.

Using pTrc-FPOX-15 as a template DNA and pairs of primers in which a codon corresponding to the amino acid to be mutated is replaced with a codon corresponding to the substituting amino acid, PCR was carried out using DNA polymerase "KOD-Plus-" of a PCR kit manufactured by TOYOBO by following the protocol provided in the kit using the following reagent composition and PCR conditions to obtain a PCR product (expression plasmid containing mutations). In the PCR reaction, the template DNA, the forward primer, and the reverse primer were used such that their concentrations in the reaction solution would be 1 to 2 mg/L, 0.3 μmol/L, and 0.3 μmol/L, respectively.

(Reagent Composition)

| | |
|---|---|
| reaction buffer | |
| template DNA | 1 to 2 ng/μL |
| forward primer | 0.3 μmol/L |
| reverse primer | 0.3 μmol/L |
| dNTP solution mixture | 0.2 mmol/L each |
| MgSO$_4$ | 1 mmol/L |
| DNA polymerase | 0.02 U/μL |
| sterilized water | added to fill up to 50 μL |

(PCR Conditions)
1. 94° C. for 2 minutes
2. 98° C. for 15 seconds
3. 60° C. for 30 seconds
4. 68° C. for 6 minutes
5. repeat 2 to 4 (for a total of 30 cycles)
6. 68° C. for 10 minutes To 50 μL of the PCR product, 1 μL of "restriction enzyme Dpn I" manufactured by New England Biolabs was added, and by incubating this at 37° C. for 1 hour, template DNA was degraded. The PCR product subjected to the restriction enzyme treatment was purified using "Wizard SV Gel and PCR Clean-Up System" manufactured by Promega, and a portion of this sample was used to transform *E. coli* competent cells "Competent high DH5α" manufactured by TOYOBO. Colonies grown on LB agar medium containing 50 mg/L ampicillin were selected, plasmids were extracted using "Wizard Plus SV Minipreps DNA Purification" manufactured by Promega, and the clones introduced with the amino acid substitutions of interest were selected by analyzing their sequences on a DNA sequencer. The primers used for the sequence analysis were primers having DNAs consisting of the nucleotide sequences represented by SEQ ID NOs: 69 and 70 which respectively reflect the nucleotide sequences just before and after the multicloning site of the pTrc99a vector (4,176-bp, manufactured by GE Healthcare Bio-Sciences), and a primer having a DNA consisting of the nucleotide sequence represented by SEQ ID NO: 71 which is the nucleotide sequence of positions 530 to 548 in the nucleotide sequence of FPOX-15 having the nucleotide sequence represented by SEQ ID NO: 35.

Each of the site-specific amino acid substitutions shown in Table 1 was introduced into the pTrc-FPOX-15 expression plasmid by the above-mentioned method to construct the glycated hemoglobin oxidase. Each of the site-specific amino acid substitutions of NOs. 1 to 19 were carried out using the respectively indicated primer pairs having the DNAs consisting of the nucleotide sequences represented by the SEQ ID NOs.

TABLE 1

| No. | Amino acid poition | Before substitution | After substitution | SEQ ID NOs of the primer pair |
|---|---|---|---|---|
| 1 | 61 | Arg | Ser | 72, 73 |
| 2 | 63 | Arg | Ala | 74, 75 |
| 3 | 62 | Leu | Gly | 76, 77 |
| 4 | 71 | Tyr | Cys | 78, 79 |
| 5 | 71 |  | Ser | 80, 81 |
| 6 | 115 | Asp | Asn | 82, 83 |
| 7 | 115 |  | Arg | 84, 85 |
| 8 | 108 | Met | Lys | 86, 87 |
| 9 | 75 | Leu | Ala | 88, 89 |
| 10 |  |  | Phe | 90, 91 |
| 11 | 34 | Ser | Thr | 92, 93 |
| 12 | 52 | Tyr | His | 94, 95 |
| 13 | 57 | Ile | Val | 96, 97 |
| 14 | 66 | Pro | His | 98, 99 |
| 15 | 95 | Asp | Glu | 100, 101 |
| 16 | 105 | Lys | Arg | 102, 103 |
| 17 | 105/108 | Lys/Lys | Arg/Arg | 102, 104 |
| 18 | 108 | Lys | Arg | 105, 106 |
| 19 | 355 | Ala | Ser | 107, 108 |

The pTrc-FPOX-18A plasmid that expresses FPOX-18A having the amino acid sequence represented by SEQ ID NO: 3 was constructed by stepwise introduction of the site-specific amino acid substitutions of Nos. 1 to 4 of Table 1 into pTrc-FPOX-15. pTrc-FPOX-18A comprises a DNA consisting of the nucleotide sequence encoding FPOX-18A represented by SEQ ID NO: 37. The pTrc-FPOX-18B plasmid that expresses FPOX-18B having the amino acid sequence represented by SEQ ID NO: 4 was constructed by stepwise introduction of the site-specific amino acid substitutions of Nos. 1 to 3 and 5 of Table 1 into pTrc-FPOX-15. pTrc-FPOX-18B comprises a DNA consisting of the nucleotide sequence encoding FPOX-18B represented by SEQ ID NO: 38. The pTrc-FPOX-18C plasmid that expresses FPOX-18C having the amino acid sequence represented by SEQ ID NO: 5 was constructed by introducing the site-specific amino acid substitution of No. 6 of Table 1 into pTrc-FPOX-18B. pTrc-FPOX-18C comprises a DNA consisting of the nucleotide sequence encoding FPOX-18C represented by SEQ ID NO: 39. The pTrc-FPOX-18D plasmid that expresses FPOX-18D having the amino acid sequence represented by SEQ ID NO: 6 was constructed by introducing the site-specific amino acid substitution of No. 7 of Table 1 into pTrc-FPOX-18B. pTrc-FPOX-18D comprises a DNA consisting of the nucleotide sequence encoding FPOX-18D represented by SEQ ID NO: 40. The pTrc-FPOX-19 plasmid that expresses FPOX-19 having the amino acid sequence represented by SEQ ID NO: 7 was constructed by introducing the site-specific amino acid substitution of No. 8 of Table 1 into pTrc-FPOX-18D. pTrc-FPOX-19 comprises a DNA consisting of the nucleotide sequence encoding FPOX-19 represented by SEQ ID NO: 41. The pTrc-FPOX-20 plasmid that expresses FPOX-20 having the amino acid sequence represented by SEQ ID NO: 8 was constructed by introducing the site-specific amino acid substitution of No. 9 of Table 1 into pTrc-FPOX-19. pTrc-FPOX-20 comprises a DNA consisting of the nucleotide sequence encoding FPOX-20 represented by SEQ ID NO: 42.

Construction of each of the expression plasmids pTrc-FPOX-21 to pTrc-FPOX-46 comprising DNAs consisting of the nucleotide sequences encoding the mutant FPOX-21 to FPOX-46 respectively having the amino acid sequences represented by SEQ ID NOs: 9 to 34 respectively was carried out by using pTrc-FPOX-19 as a template, and by performing stepwise introduction of a combination of the site-specific mutations of Nos. 10 to 19 in Table 1 and accumulating the mutations as indicated in Table 2.

TABLE 2

Amino acid mutation(s) based on FPOX-19

| Mutant | Position(s) of mutation and amino acids before and after substitution | No. in Table 1 |
|---|---|---|
| FPOX-21 | L75F | 10 |
| FPOX-22 | L75F/S34T | 10, 11 |
| FPOX-23 | L75F/Y52H | 10, 12 |
| FPOX-24 | L75F/I57V | 10, 13 |
| FPOX-25 | L75F/P66H | 10, 14 |
| FPOX-26 | L75F/D95E | 10, 15 |
| FPOX-27 | L75F/K105R | 10, 16 |
| FPOX-28 | L75F/K108R | 10, 18 |
| FPOX-29 | L75F/A355S | 10, 19 |
| FPOX-30 | L75F/P66H/D95E | 10, 14, 15 |
| FPOX-31 | L75F/P66H/D95E/K105R | 10, 14, 15, 16 |
| FPOX-32 | L75F/P66H/D95E/K105R/K108R | 10, 14, 15, 17 |
| FPOX-33 | L75F/P66H/D95E/K105R/K108R/S34T | 10, 11, 14, 15, 17 |
| FPOX-34 | L75F/P66H/D95E/K105R/K108R/Y52H | 10, 12, 14, 15, 17 |
| FPOX-35 | L75F/P66H/D95E/K105R/K108R/I57V | 10, 13, 14, 15, 17 |
| FPOX-36 | L75F/P66H/K108R | 10, 14, 18 |
| FPOX-37 | L75F/P66H/K105R/K108R | 10, 14, 17 |
| FPOX-38 | L75F/P66H/A355S | 10, 14, 19 |
| FPOX-39 | L75F/P66H/A355S/D95E | 10, 14, 15, 19 |
| FPOX-40 | L75F/P66H/A355S/K105R | 10, 14, 16, 19 |
| FPOX-41 | L75F/P66H/A355S/K108R | 10, 14, 18, 19 |
| FPOX-42 | L75F/P66H/K105R/K108R/A355S | 10, 14, 17, 19 |
| FPOX-43 | L75F/P66H/K105R/K108R/A355S/S34T | 10, 11, 14, 17, 19 |
| FPOX-44 | L75F/P66H/K105R/K108R/A355S/Y52H | 10, 12, 14, 17, 19 |
| FPOX-45 | L75F/P66H/K105R/K108R/A355S/I57V | 10, 13, 14, 17, 19 |
| FPOX-46 | L75F/P66H/K105R/K108R/A355S/D95E | 10, 14, 15, 17, 19 |

Transformant E. coli strains expressing each of the glycated hemoglobin oxidases were produced by transforming the E. coli DH5α strain by introducing each of the 32 types of glycated hemoglobin oxidase expression plasmids described above, which are pTrc-FPOX-18A, pTrc-FPOX-18B, pTrc-FPOX-18C, pTrc-FPOX-18D, and pTrc-FPOX-19 to pTrc-FPOX-46.

Among the glycated hemoglobin oxidase-expressing E. coli strains obtained above, E. coli strains expressing each of the proteins FPOX-19, FPOX-20, FPOX-32, and FPOX-42 were used, and by following the glycated peptide oxidase expression and purification methods described in International Publication WO 2010/041715, the glycated hemoglobin oxidases were purified, and were used for the methods for measuring glycated hemoglobin of the present invention.

The protein concentrations of the purified glycated hemoglobin oxidases were determined by the following method based on FAD harbored by glycated hemoglobin oxidases.

First, glycated peptide oxidase FPOX-CE (manufactured by Kikkoman Co.) was diluted using 10 mmol/L phosphate buffer (pH7.0) to prepare FPOX-CE solutions having each of the following concentrations: 0.7, 1.4, 2.8, 5.6, and 11.2 mg/mL. The FPOX-CE solutions prepared at each of the concentrations, were subjected to absorbance measurements at 452 nm (main wavelength)/600 nm (sub-wavelength) using the "Ultrospec 2100 pro" spectrophotometer manufactured by GE Healthcare to produce a calibration curve indicating the relationship between FPOX-CE concentration and absorbance. Next, purified glycated hemoglobin oxidase was used as a sample instead of the aforementioned FPOX-CE, but otherwise the same method was used to measure the absorbance of the purified protein. Protein concentrations of the purified glycated hemoglobin oxidases were determined by comparing the measured absorbance values with the values of the above-described calibration curve.

[Example 2] Correlation Between the Method of the Present Invention for Measuring Glycated Hemoglobin and the Method for Measuring Glycated Hemoglobin that Uses the HPLC Method (KO500 Method) and the Hemoglobin-SLS Method Using each of the mutants FPOX-19, FPOX-20, FPOX-32, and FPOX-42 obtained in Example 1 as an enzyme, and using hemolysate samples derived from human blood cells, whose HbA1c concentrations have been determined by both of the HPLC method (KO500 method) and the hemoglobin-SLS method, as a test sample, the change in absorbance for each of the samples was determined using the following reagents and measurement procedure. In the measurement of hemoglobin concentration by the hemoglobin-SLS method, Hemoglobin B-test Wako (manufactured by Wako Pure Chemical Industries) was used.

(Reagents for Activity Measurement)
Solution A: 0.1 mol/L MOPS buffer (pH6.8)
Solution B: 24 mmol/L DA-67 solution in DMF
Solution C: 1 kU/L peroxidase solution in 10 mmol/L phosphate buffer (pH7.0)
Solution D: hemolysate samples derived from human blood cells [hemoglobin concentration is 10 mg/mL, and the HbA1c concentrations have been given values of 9.8, 11.1, 12.3, 13.3, 14.5, 15.4, 17.9, and 23.3 µmol/L from both of the HPLC method (KO500 method) and the hemoglobin-SLS method]
Solution E: aqueous solution of 5 g/L potassium iodate and 50% (v/v) AMPHITOL 20N
Solution F: 40 mg/mL glycated hemoglobin oxidase (each of the mutants FPOX-19, FPOX-20, FPOX-32, and FPOX-42) solution in 10 mmol/L phosphate buffer (pH7.0)
(Measurement Procedure)
(i) 4 µL of Solution E was added to 40 µL of Solution D and mixed, and the mixture was incubated at 37° C. for 10 minutes.
(ii) To 10 mL of Solution A, 12.6 µL of Solution B and 35 µL of Solution C were added, the obtained solution was dispensed into each well of a 96-well microplate at 190 µL per sample, then 40 µL of a solution produced by mixing Solutions D and E, and 20 µL of Solution F were added and mixed, and this was allowed to react at 37° C. for 60 minutes.

The absorbance of the solution before reaction $Abs_{(before\ reaction)}$ at 660 nm (main wavelength)/750 nm (sub-wavelength), and the absorbance of the solution after reaction $Abs_{(after\ reaction)}$ at 660 nm (main wavelength)/750 nm (sub-wavelength) were measured using a fully automated microplate EIA analyzer (AP-96, manufactured by Kyowa Medex Co., Ltd.). The absorbance change due to the reaction $\Delta'Abs_{(reaction)}$ was determined by subtracting the absorbance $Abs_{(before\ reaction)}$ from the absorbance $Abs_{(after\ reaction)}$.

Similar measurements were performed using two hemolysate samples derived from human blood cells which have known HbA1c concentrations (samples in which hemoglobin concentration is 10 mg/mL and the HbA1c concentrations are 9.82 µmol/L and 24.2 µmol/L, respectively) to prepare a calibration curve indicating the relationship between HbA1c concentration and absorbance change due to the reaction $\Delta'Abs_{(reaction)}$.

HbA1c concentration in each of the hemolysate samples derived from human blood cells was determined by correlating the absorbance change due to the reaction $\Delta'Abs_{(reaction)}$ values for each of the hemolysate samples derived from human blood cells to the values of the above-mentioned calibration curve. HbA1c concentration determined this way was compared with the HbA1c concentration determined by the control method using both of the HPLC method (KO500 method) and the hemoglobin-SLS method.

Figure 2:
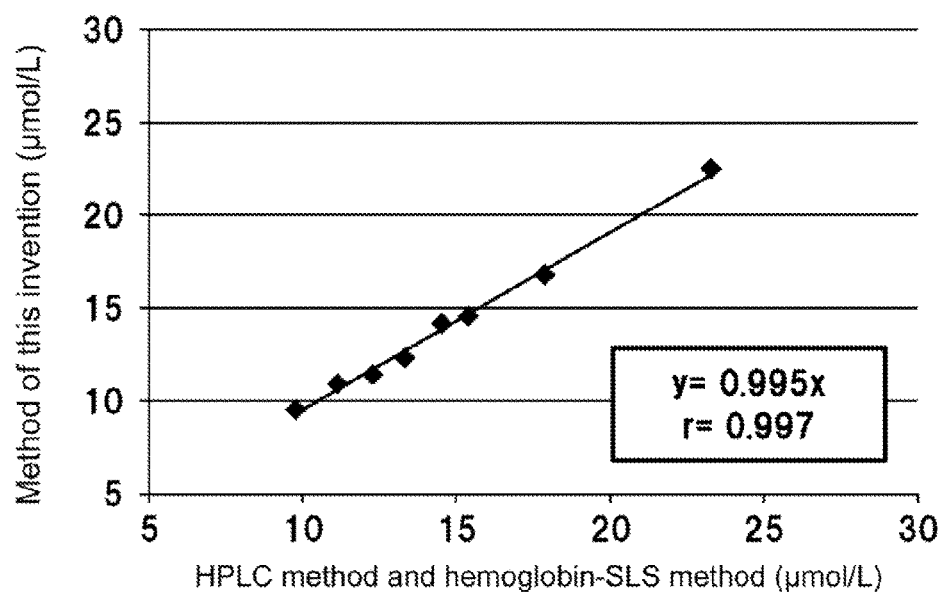
FIG. 2 shows a graph indicating the correlation between HbA1c concentrations determined by the HbA1c measurement method of the present invention which directly oxidizes HbA1c using FPOX-20, and HbA1c concentrations determined by the HbA1c measurement method that uses both of the HPLC method (KO500 method) and the hemoglobin-SLS method.
Figure 3:
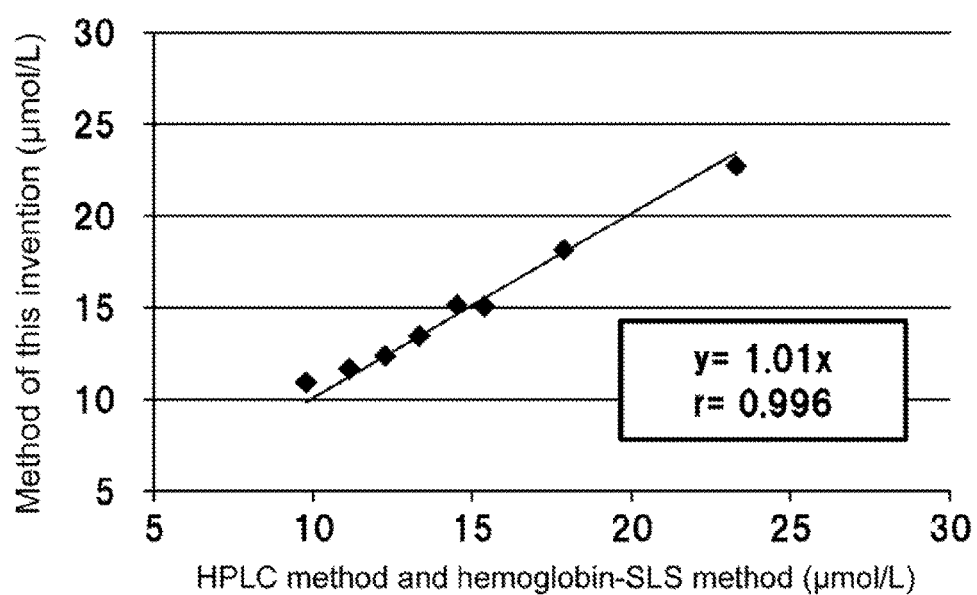
FIG. 3 shows a graph indicating the correlation between HbA1c concentrations determined by the HbA1c measurement method of the present invention which directly oxidizes HbA1c using FPOX-32, and HbA1c concentrations determined by the HbA1c measurement method that uses both of the HPLC method (KO500 method) and the hemoglobin-SLS method.
Figure 4:
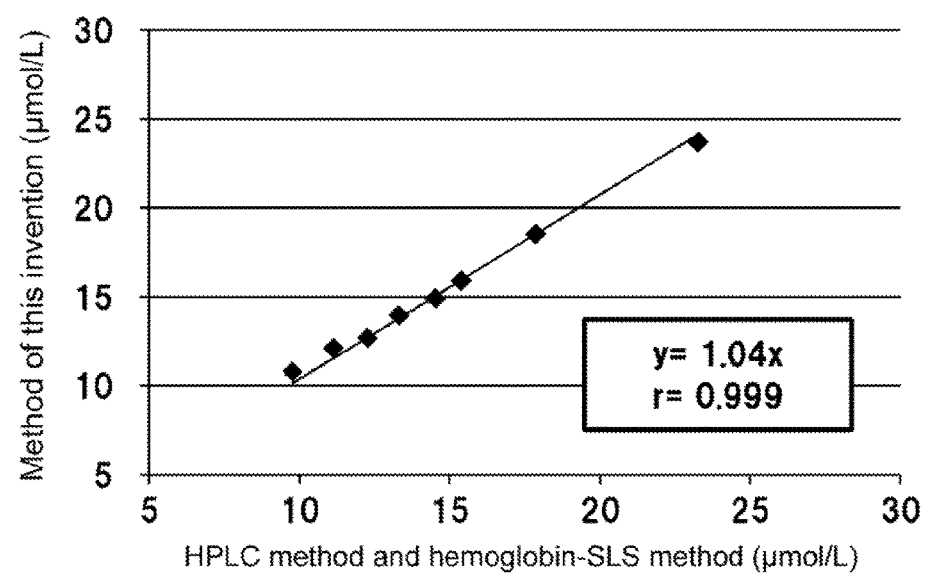
FIG. 4 shows a graph indicating the correlation between HbA1c concentrations determined by the HbA1c measurement method of the present invention which directly oxidizes HbA1c using FPOX-42, and HbA1c concentrations determined by the HbA1c measurement method that uses both of the HPLC method (KO500 method) and the hemoglobin-SLS method.

As shown in FIGS. 1 to 4, good correlation was observed between HbA1c concentrations determined by the measurement method of the present invention and HbA1c concentrations determined by the control method using both of the HPLC method (KO500 method) and the hemoglobin-SLS method. Accordingly, the measurement method of the present invention was found to be able to measure HbA1c in samples.

INDUSTRIAL APPLICABILITY

The present invention provides a method for measuring glycated hemoglobin, which is useful for diagnosing lifestyle-related disease such as diabetes mellitus.

SEQUENCE LISTING FREE TEXT

SEQ ID NO: 1—Description of Artificial Sequence: Amino acid sequence of FPOX-15
SEQ ID NO: 2—Description of Artificial Sequence: Amino acid sequence of FPOX-9
SEQ ID NO: 3—Description of Artificial Sequence: Amino acid sequence of FPOX-18A
SEQ ID NO: 4—Description of Artificial Sequence: Amino acid sequence of FPOX-18B
SEQ ID NO: 5—Description of Artificial Sequence: Amino acid sequence of FPOX-18C
SEQ ID NO: 6—Description of Artificial Sequence: Amino acid sequence of FPOX-18D
SEQ ID NO: 7—Description of Artificial Sequence: Amino acid sequence of FPOX-19
SEQ ID NO: 8—Description of Artificial Sequence: Amino acid sequence of FPOX-20
SEQ ID NO: 9—Description of Artificial Sequence: Amino acid sequence of FPOX-21
SEQ ID NO: 10—Description of Artificial Sequence: Amino acid sequence of FPOX-22
SEQ ID NO: 11—Description of Artificial Sequence: Amino acid sequence of FPOX-23
SEQ ID NO: 12—Description of Artificial Sequence: Amino acid sequence of FPOX-24

SEQ ID NO: 13—Description of Artificial Sequence: Amino acid sequence of FPOX-25
SEQ ID NO: 14—Description of Artificial Sequence: Amino acid sequence of FPOX-26
SEQ ID NO: 15—Description of Artificial Sequence: Amino acid sequence of FPOX-27
SEQ ID NO: 16—Description of Artificial Sequence: Amino acid sequence of FPOX-28
SEQ ID NO: 17—Description of Artificial Sequence: Amino acid sequence of FPOX-29
SEQ ID NO: 18—Description of Artificial Sequence: Amino acid sequence of FPOX-30
SEQ ID NO: 19—Description of Artificial Sequence: Amino acid sequence of FPOX-31
SEQ ID NO: 20—Description of Artificial Sequence: Amino acid sequence of FPOX-32
SEQ ID NO: 21—Description of Artificial Sequence: Amino acid sequence of FPOX-33
SEQ ID NO: 22—Description of Artificial Sequence: Amino acid sequence of FPOX-34
SEQ ID NO: 23—Description of Artificial Sequence: Amino acid sequence of FPOX-35
SEQ ID NO: 24—Description of Artificial Sequence: Amino acid sequence of FPOX-36
SEQ ID NO: 25—Description of Artificial Sequence: Amino acid sequence of FPOX-37
SEQ ID NO: 26—Description of Artificial Sequence: Amino acid sequence of FPOX-38
SEQ ID NO: 27—Description of Artificial Sequence: Amino acid sequence of FPOX-39
SEQ ID NO: 28—Description of Artificial Sequence: Amino acid sequence of FPOX-40
SEQ ID NO: 29—Description of Artificial Sequence: Amino acid sequence of FPOX-41
SEQ ID NO: 30—Description of Artificial Sequence: Amino acid sequence of FPOX-42
SEQ ID NO: 31—Description of Artificial Sequence: Amino acid sequence of FPOX-43
SEQ ID NO: 32—Description of Artificial Sequence: Amino acid sequence of FPOX-44
SEQ ID NO: 33—Description of Artificial Sequence: Amino acid sequence of FPOX-45
SEQ ID NO: 34—Description of Artificial Sequence: Amino acid sequence of FPOX-46
SEQ ID NO: 35—Description of Artificial Sequence: DNA of FPOX-15
SEQ ID NO: 36—Description of Artificial Sequence: DNA of FPOX-9
SEQ ID NO: 37—Description of Artificial Sequence: DNA of FPOX-18A
SEQ ID NO: 38—Description of Artificial Sequence: DNA of FPOX-18B
SEQ ID NO: 39—Description of Artificial Sequence: DNA of FPOX-18C
SEQ ID NO: 40—Description of Artificial Sequence: DNA of FPOX-18D
SEQ ID NO: 41—Description of Artificial Sequence: DNA of FPOX-19
SEQ ID NO: 42—Description of Artificial Sequence: DNA of FPOX-20
SEQ ID NO: 43—Description of Artificial Sequence: DNA of FPOX-21
SEQ ID NO: 44—Description of Artificial Sequence: DNA of FPOX-22
SEQ ID NO: 45—Description of Artificial Sequence: DNA of FPOX-23
SEQ ID NO: 46—Description of Artificial Sequence: DNA of FPOX-24
SEQ ID NO: 47—Description of Artificial Sequence: DNA of FPOX-25
SEQ ID NO: 48—Description of Artificial Sequence: DNA of FPOX-26
SEQ ID NO: 49—Description of Artificial Sequence: DNA of FPOX-27
SEQ ID NO: 50—Description of Artificial Sequence: DNA of FPOX-28
SEQ ID NO: 51—Description of Artificial Sequence: DNA of FPOX-29
SEQ ID NO: 52—Description of Artificial Sequence: DNA of FPOX-30
SEQ ID NO: 53—Description of Artificial Sequence: DNA of FPOX-31
SEQ ID NO: 54—Description of Artificial Sequence: DNA of FPOX-32
SEQ ID NO: 55—Description of Artificial Sequence: DNA of FPOX-33
SEQ ID NO: 56—Description of Artificial Sequence: DNA of FPOX-34
SEQ ID NO: 57—Description of Artificial Sequence: DNA of FPOX-35
SEQ ID NO: 58—Description of Artificial Sequence: DNA of FPOX-36
SEQ ID NO: 59—Description of Artificial Sequence: DNA of FPOX-37
SEQ ID NO: 60—Description of Artificial Sequence: DNA of FPOX-38
SEQ ID NO: 61—Description of Artificial Sequence: DNA of FPOX-39
SEQ ID NO: 62—Description of Artificial Sequence: DNA of FPOX-40
SEQ ID NO: 63—Description of Artificial Sequence: DNA of FPOX-41
SEQ ID NO: 64—Description of Artificial Sequence: DNA of FPOX-42
SEQ ID NO: 65—Description of Artificial Sequence: DNA of FPOX-43
SEQ ID NO: 66—Description of Artificial Sequence: DNA of FPOX-44
SEQ ID NO: 67—Description of Artificial Sequence: DNA of FPOX-45
SEQ ID NO: 68—Description of Artificial Sequence: DNA of FPOX-46
SEQ ID NO: 69—Description of Artificial Sequence: pTrc-F1 primer
SEQ ID NO: 70—Description of Artificial Sequence: pTrc-R primer
SEQ ID NO: 71—Description of Artificial Sequence: pTrc-F2 primer
SEQ ID NO: 72—Description of Artificial Sequence: R61S-F primer
SEQ ID NO: 73—Description of Artificial Sequence: R61S-R primer
SEQ ID NO: 74—Description of Artificial Sequence: R63A-F primer
SEQ ID NO: 75—Description of Artificial Sequence: R63A-R primer
SEQ ID NO: 76—Description of Artificial Sequence: L62G-F primer
SEQ ID NO: 77—Description of Artificial Sequence: L62G-R primer
SEQ ID NO: 78—Description of Artificial Sequence: Y71C-F primer SEQ ID NO: 79—Description of Artificial Sequence: Y71C-R primer
SEQ ID NO: 80—Description of Artificial Sequence: Y71S-F primer
SEQ ID NO: 81—Description of Artificial Sequence: Y71S-R primer
SEQ ID NO: 82—Description of Artificial Sequence: D115N-F primer
SEQ ID NO: 83—Description of Artificial Sequence: D115N-R primer
SEQ ID NO: 84—Description of Artificial Sequence: D115R-F primer
SEQ ID NO: 85—Description of Artificial Sequence: D115R-R primer
SEQ ID NO: 86—Description of Artificial Sequence: M108K-F primer
SEQ ID NO: 87—Description of Artificial Sequence: M108K-R primer
SEQ ID NO: 88—Description of Artificial Sequence: L75A-F primer
SEQ ID NO: 89—Description of Artificial Sequence: L75A-R primer
SEQ ID NO: 90—Description of Artificial Sequence: L75F-F primer
SEQ ID NO: 91—Description of Artificial Sequence: L75F-R primer
SEQ ID NO: 92—Description of Artificial Sequence: S34T-F primer
SEQ ID NO: 93—Description of Artificial Sequence: S34T-R primer
SEQ ID NO: 94—Description of Artificial Sequence: Y52H-F primer
SEQ ID NO: 95—Description of Artificial Sequence: Y52H-R primer
SEQ ID NO: 96—Description of Artificial Sequence: I57V-F primer
SEQ ID NO: 97—Description of Artificial Sequence: I57V-R primer
SEQ ID NO: 98—Description of Artificial Sequence: P66H-F primer
SEQ ID NO: 99—Description of Artificial Sequence: P66H-R primer
SEQ ID NO: 100—Description of Artificial Sequence: D95E-F primer
SEQ ID NO: 101—Description of Artificial Sequence: D95E-R primer
SEQ ID NO: 102—Description of Artificial Sequence: K105R-F primer
SEQ ID NO: 103—Description of Artificial Sequence: K105R-R1 primer
SEQ ID NO: 104—Description of Artificial Sequence: K105R-R2 primer
SEQ ID NO: 105—Description of Artificial Sequence: K108R-F primer
SEQ ID NO: 106—Description of Artificial Sequence: K108R-R primer
SEQ ID NO: 107—Description of Artificial Sequence: A355S-F primer
SEQ ID NO: 108—Description of Artificial Sequence: A355S-R primer

The invention claimed is:

1. A method for measuring glycated hemoglobin in a sample, wherein the method comprises:
   (i) contacting glycated hemoglobin in the sample with an enzyme that directly oxidizes glycated hemoglobin, wherein the glycated hemoglobin is not degraded by a protease; and
   (ii) measuring a substance produced or consumed in step (i).

2. The method of claim 1, wherein the produced substance is hydrogen peroxide.

3. The method of claim 1, wherein the glycated hemoglobin is hemoglobin A1c.

4. The method of claim 2, wherein the glycated hemoglobin is hemoglobin A1c.

* * * * *